(12) United States Patent
McGill et al.

(10) Patent No.: US 11,654,415 B2
(45) Date of Patent: May 23, 2023

(54) BISPHENOL HYPERSORBENTS FOR ENHANCED DETECTION OF, OR PROTECTION FROM, HAZARDOUS CHEMICALS

(71) Applicant: The Government of the United States of America, as represented by the Secretary of the Navy, Arlington, VA (US)

(72) Inventors: R. Andrew McGill, Lorton, VA (US); Courtney A. Roberts, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 17/725,794

(22) Filed: Apr. 21, 2022

(65) Prior Publication Data
US 2022/0258125 A1    Aug. 18, 2022

Related U.S. Application Data

(62) Division of application No. 16/178,488, filed on Nov. 1, 2018, now Pat. No. 11,325,100.

(Continued)

(51) Int. Cl.
*B01J 20/00*    (2006.01)
*B01J 20/22*    (2006.01)
(Continued)

(52) U.S. Cl.
CPC ............. *B01J 20/22* (2013.01); *B01J 20/281* (2013.01); *B01J 20/282* (2013.01);
(Continued)

(58) Field of Classification Search
CPC ........................................................ B01J 20/22
(Continued)

(56) References Cited

U.S. PATENT DOCUMENTS

| 6,015,869 A | 1/2000 | Grate et al. |
| 2017/0184531 A1 | 6/2017 | Snelders et al. |

OTHER PUBLICATIONS

Abraham et al. "Hydrogen Bonding. Part 18.t Gas-Liquid Chromatographic Measurements for the Design and Selection of some Hydrogen Bond Acidic Phases Suitable for Use as Coatings on Piezoelectric Sorption Detectors" J. Chem. Soc. Perkin Trans. 2 1991 (Year: 1991).*

(Continued)

*Primary Examiner* — Christine T Mui
*Assistant Examiner* — Emily R. Berkeley
(74) *Attorney, Agent, or Firm* — US Naval Research Laboratory; Roy Roberts

(57) ABSTRACT

The invention relates to strong hydrogen-bond acidic sorbents. The sorbents may be provided in a form that limits or eliminates intramolecular bonding of the hydrogen-bond acidic site between neighboring sorbent molecules, for example, by providing steric groups adjacent to the hydrogen-bond acidic site. The hydrogen bond site may be a phenolic structure based on a bisphenol architecture. The sorbents of the invention may be used in methods for trapping or detecting hazardous chemicals or explosives.

6 Claims, 19 Drawing Sheets

Related U.S. Application Data

(60) Provisional application No. 62/582,038, filed on Nov. 6, 2017.

(51) Int. Cl.

| | |
|---|---|
| *B01J 20/282* | (2006.01) |
| *B01J 20/28* | (2006.01) |
| *B01J 20/34* | (2006.01) |
| *C08G 59/00* | (2006.01) |
| *C08F 14/06* | (2006.01) |
| *C07C 39/367* | (2006.01) |
| *B01J 20/281* | (2006.01) |
| *C08G 64/00* | (2006.01) |
| *C08G 64/10* | (2006.01) |

(52) U.S. Cl.
CPC ..... *B01J 20/28023* (2013.01); *B01J 20/3425* (2013.01); *B01J 20/3483* (2013.01); *C07C 39/367* (2013.01); *C08F 14/06* (2013.01); *C08G 59/00* (2013.01); *C08G 64/00* (2013.01); *C08G 64/10* (2013.01); *G01N 30/482* (2013.01); *B01J 2220/54* (2013.01)

(58) Field of Classification Search
USPC .......................................................... 436/98
See application file for complete search history.

(56) References Cited

OTHER PUBLICATIONS

Hartmann-Thompson et al. "Hydrogen-Bond Acidic Polyhedral Oligosilsesquioxane Filled Polymer Coatings for Surface Acoustic Wave Sensors" J. Appl. Polym. Sci., 104: 3171-3182 (2007) (Year: 2007).*

International Search Report and Opinion dated Mar. 6, 2019 in PCT/US2018/05880.

Lau, K.-T. et al, Sensors and Actuators B, 1998, vol. 50, pp. 69-79.

Grate, J.W. et al., Analytical Chemistry, Mar. 1, 1999, vol. 71, No. 5, pp. 1033-1040.

Levitsky, I. Analytical Chemistry Jul. 15, 2001, vol. 73, No. 14, pp. 3441-3448.

* cited by examiner

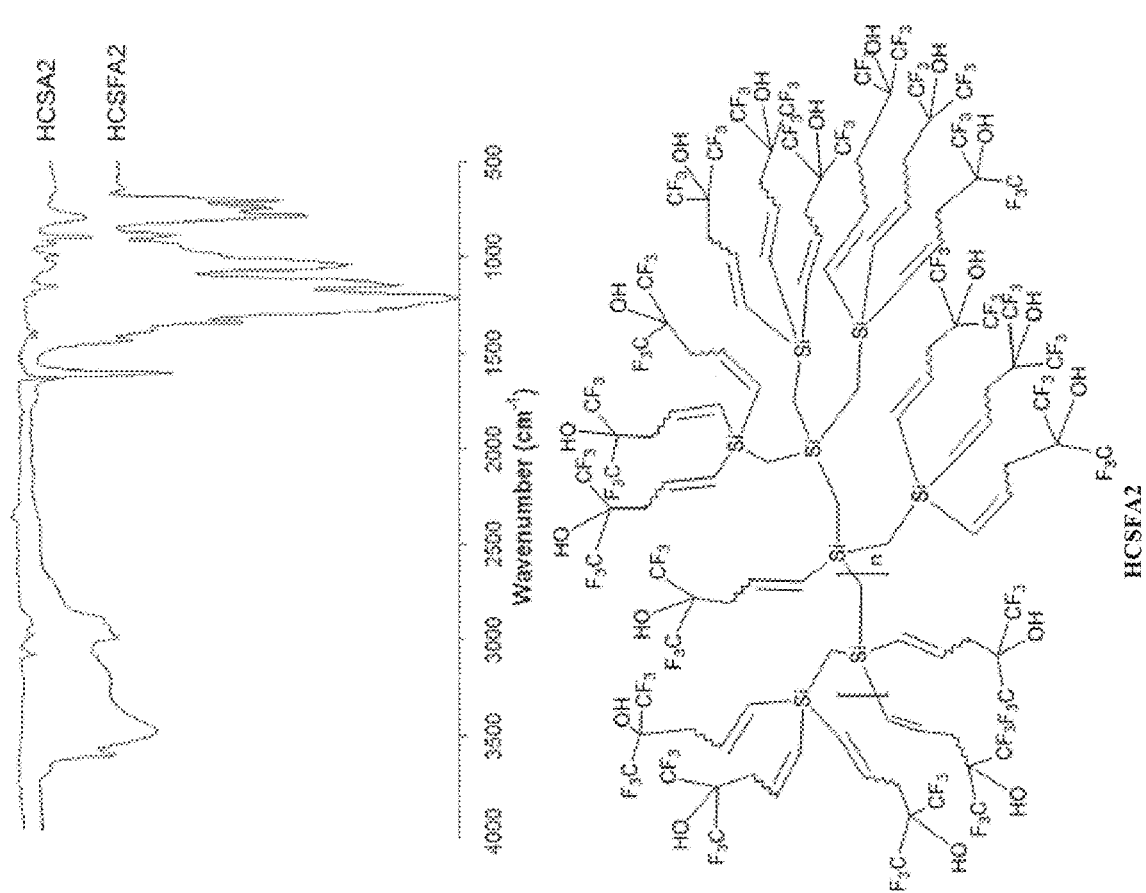

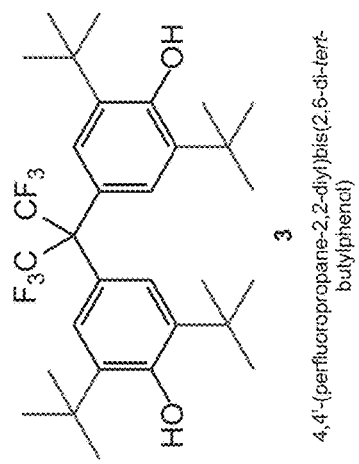
FIG. 2A
4,4'-(perfluoropropane-2,2-diyl)bis(2,6-di-*tert*-butylphenol)
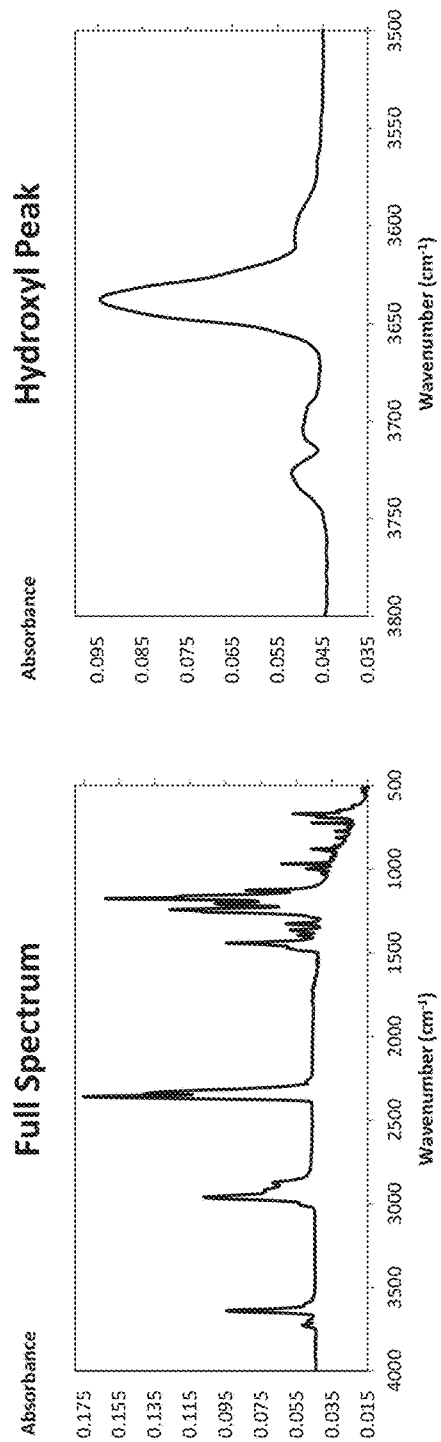
FIG. 2B
FIG. 2C

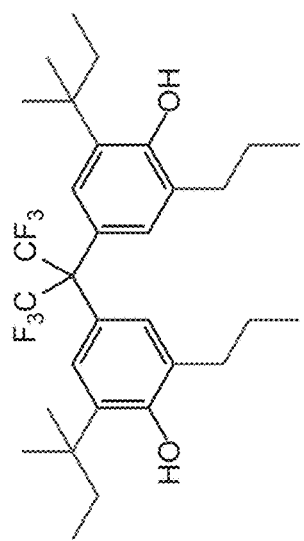
FIG. 3A
4,4'-(perfluoropropane-2,2-diyl)bis(2-(tert-pentyl)-6-propylphenol)
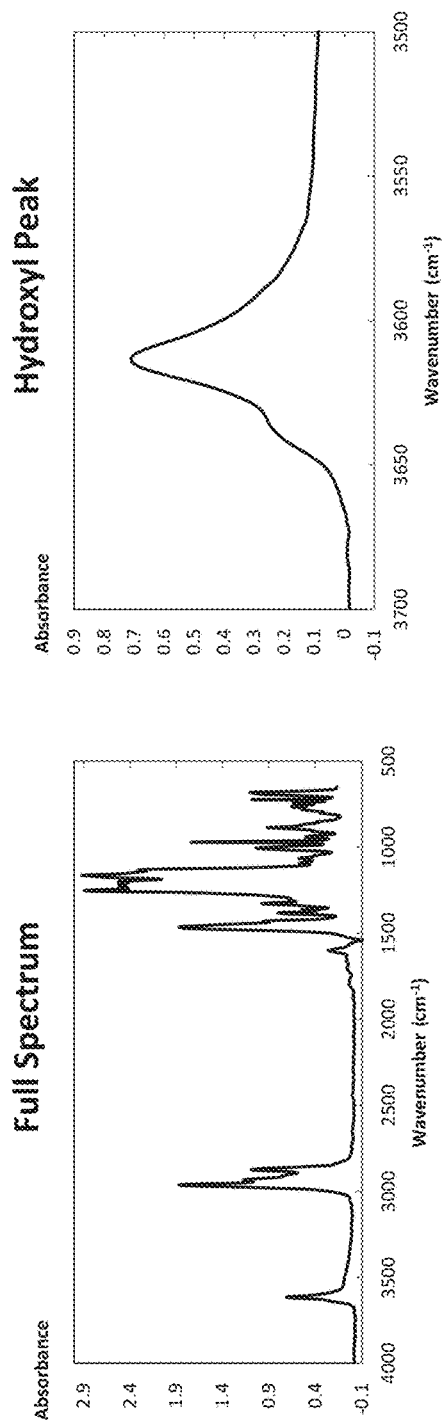
FIG. 3B
FIG. 3C

Scheme 1. Synthesis of 4,4'-[2,2,2-Trifluoro-1-(trifluoromethyl)ethylidene]bis[2,6-diisopropylphenol] 2.

Scheme 2. Synthesis of 4,4'-[2,2,2-Trifluoro-1-(trifluoromethyl)ethylidene]bis[2,6-di-*tert*-butylphenol] 3.

Scheme 3. Synthesis of 4,4'-(Perfluoropropane-2,2-diyl)bis(2-(*tert*-pentyl)phenol) 7.

Scheme 4. Synthesis of 4,4'-(Perfluoropropane-2,2-diyl)bis(2-allyl-6-(tert-pentyl)phenol) 10.

Scheme 5. Synthesis of 4,4'-(Perfluoropropane-2,2-diyl)bis(2-allyl-6-propylphenol) 14.

Scheme 6. Planned synthesis of 4,4'-(perfluoropropane-2,2-diyl)bis(2,6-diethylphenol) 19.

Scheme 7. Planned synthesis of 4,4'-(perfluoropropane-2,2-diyl)bis(2-ethyl-6-(tert-pentyl)phenol) 24.

Scheme 8. Planned synthesis of 4,4'-(perfluoropropane-2,2-diyl)bis(2,6-di-tert-pentylphenol) 28.

Scheme 9. Planned synthesis of 4,4'-(perfluoropropane-2,2-diyl)bis(2-isopropyl-6-(tert-pentyl)phenol) 29.

Scheme 10. Summary of bisphenol sorbents.

BISPHENOL HYPERSORBENTS FOR ENHANCED DETECTION OF, OR PROTECTION FROM, HAZARDOUS CHEMICALS

CROSS-REFERENCE TO RELATED APPLICATIONS

This application claims the benefit as a division of U.S. patent application Ser. No. 16/178,488 filed on Nov. 1, 2018 which in turn claims priority to U.S. Provisional Application No. 62/582,038, filed on Nov. 6, 2017, the contents of each of which is incorporated herein by reference in its entirety.

FIELD OF THE INVENTION

This application relates generally to strong hydrogen-bond acidic sorbents. The sorbents may be provided in a form that limits or eliminates intermolecular bonding of one or more hydrogen-bond acidic site(s) between neighboring sorbent molecules, for example, by providing steric groups adjacent to the hydrogen-bond acidic site. The hydrogen-bond site may be a phenolic structure based on a bisphenol architecture. The sorbents of the invention may be used in methods for the detection, chromatographic separation, and trapping of hazardous chemicals, explosives, or related chemicals.

BACKGROUND OF THE INVENTION

Hypersorbents for targeting hydrogen-bond basic chemicals primarily consist of polymers with carbosilane, siloxane, or ether linked backbones that have been functionalized with strong hydrogen-bond acidic groups to reversibly bind complimentary hydrogen-bond basic chemicals. Previously developed exemplary sorbents include fluoropolyol (FPOL), poly(oxy{methyl[4-hydroxy-4,4,bis(trifluoromethyl)but-1-en-1yl]silylene}) (SXFA), poly(oxy {bis[4-hydroxy-4,4,bis(trifluoromethyl)but-1-en-1-yl]silylene}) (SXFA2), and poly(methyldi(1,1,1-trifluoro-2-trifluoromethyl-2-hydroxypent4-enyl)silane (HCFSA2, a hyper-branched carbosilane fluoroalcohol-based sorbent polymer). Hexafluoroisopropanol groups are common motifs, included for example, in SXFA, SXFA2 and HCSFA2 sorbents. The trifluoromethyl groups augment the hydrogen-bond acidity of the sorbents, which increases the interactions with hydrogen-bond basic analytes of interest. In addition, they reduce the hydrogen-bond basicity of the oxygen atom in the hydroxyl by withdrawing electron density away from the oxygen.

However, a significant drawback to these and related sorbents with hydroxyl moieties is the propensity for self-association. This self-association, and to an extent the degree of self-association, can be qualitatively or quantitatively assessed by infrared spectroscopy. For example, FIGS. 1A and 1B show the propensity of HCSFA2 to self-associate. There is only a small amount of free hydroxyl (—OH) visible, with most of the molecules' hydroxyl groups bonded to other groups within the same sorbent molecule, or to other sorbent molecules. The existence of sorbent-sorbent hydrogen bonding, in any one instant, leads to a decrease in available sorbent-analyte binding sites, sorption kinetics, and overall sorbent efficacy.

Accordingly, there is a need in the art for sorbents having binding sites that are available to form sorbent-analyte bonds, and steric groups that are able to prevent self-association among sorbents while still permitting sorbent-analyte binding.

SUMMARY OF THE INVENTION

The invention described herein, including the various aspects and/or embodiments thereof, meets the unmet needs of the art, as well as others, by providing strong hydrogen-bond acidic sorbents. The sorbents may be provided in a form that limits or eliminates intra- or inter-molecular bonding of one or more hydrogen-bond acidic site(s) within a sorbent molecule, or between neighboring sorbent molecules, for example, by providing steric groups adjacent to the hydrogen-bond acidic site. The hydrogen-bond site may be a phenolic structure based on a bisphenol architecture. The sorbents of the invention may be used in methods for detecting, chromatographic separations, and trapping hazardous chemicals, explosives, or related chemicals.

In one aspect of the invention, a bisphenol sorbent is provided that includes a compound of Formula I

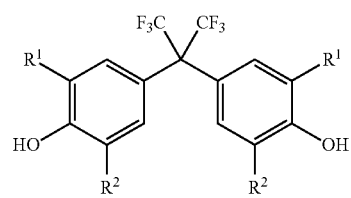

where $R^1$ is selected from the group consisting of prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethyl silyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl (methyl)amino; benzoyl amino; 2-propenyl; prop-2-enyl; triethylgermyl; benzyl; isobutyramido; (ethylcarbamothioyl)amino; bis(dimethylamino) phosphaneyl; hydroxy; 4-methoxyphenyl; (diethoxyphosphoryl)methyl; ethylthio; diphenylamino; (methoxy carbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl) amino; 2-methylpropyl; phenylethyl; propyl; butyl; sec-butyl; (butoxycarbonyl)amino; pentyl; heptyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; cyclobutyl; 3-ethylpentan-3-yl; ethyl; 1,1-dimethylpropyl; (trimethylsilyl)oxy; prop-2-enoxy; phenylamino; ((trimethylsilyl)oxy) methyl; (trimethylsilyl)methyl; methoxy; hydroxy amino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy)1; carboxylate; (hydroxyoxidophosphoryl)oxy; propan-1-id-3-yl; nitroamido; trihydroxyborato; sulfido; oxidomethoxy; oxido; trifluoromethyl; and fluoro; and $R^2$ is selected from the group consisting of hydrogen, prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl(methyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; cyclobutyl; 3-ethylpentan-3-yl; ethyl; 1,1-dimethylpropyl; (trimethyl silyl)oxy; prop-2-enoxy; phenylamino; ((trimethylsilyl)oxy)methyl; (trimethylsilyl)methyl; methoxy; hydroxyamino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy)1; carboxylate; (hydroxyoxidophosphoryl)oxy; propan-1-id-3-yl; nitroamido; trihydroxyborato; sulfido; oxidomethoxy; oxido; trifluoromethyl; and fluoro.

In another aspect of the invention, a bisphenol sorbent is provided that includes a compound of Formula II

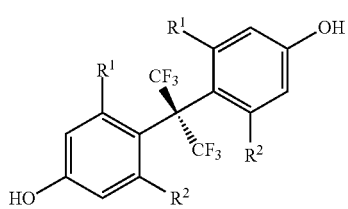

where $R^1$ is selected from the group consisting of prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl (m ethyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenylamino; ((trimethyl silyl)oxy)methyl; (trimethylsilyl)methyl; methoxy; hydroxy amino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy) 1; carboxylate; (hydroxyoxidophosphoryl)oxy; propan-1d-3-yl; nitroamido; trihydroxyborato; sulfido; oxidomethoxy; oxido; trifluoromethyl; and fluoro; and $R^2$ is selected from the group consisting of hydrogen, prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl(methyl)amino; benzoylamino; 2-propenyl; prop-2-enyl; triethylgermyl; benzyl; isobutyramido; (ethylcarbamothioyl)amino; bis(dimethylamino) phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenyl amino; ((trimethylsilyl)oxy)methyl; (trimethylsilyl)methyl; methoxy; hydroxy amino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy)1; carboxylate; (hydroxyoxidophosphoryl)oxy; propan-1-id-3-yl; nitroamido; trihydroxyborato; sulfido; oxidomethoxy; oxido; trifluoromethyl; and fluoro.

In a further aspect of the invention, a method for detecting an analyte having one or more hydrogen-bond basic groups is provided, including: providing a bisphenol sorbent of Formula I or Formula II having steric groups $R^1$ and $R^2$,

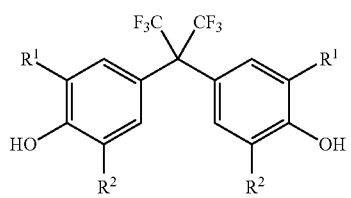

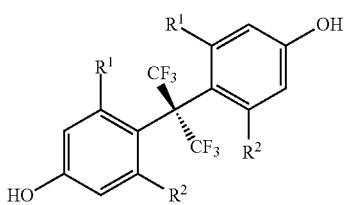

wherein $R^1$ is selected from the group consisting of prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl (methyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenylamino; ((trimethylsilyl)oxy)methyl; (trimethylsilyl)methyl; methoxy; hydroxy amino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy)1; carboxylate; (hydroxyoxidophosphoryl)oxy; propan-1-id-3-yl; nitroamido; trihydroxyborato; sulfido; oxidomethoxy; oxido; trifluoromethyl; and fluoro; and $R^2$ is selected from the group consisting of hydrogen, prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl(methyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenylamino; ((trimethyl silyl)oxy)methyl; (trimethylsilyl)methyl; methoxy; hydroxy amino; 3,3-dimethylethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy)1; carboxylate; (hydroxyoxidophosphoryl)oxy; propan-1-id-3-yl; nitroamido; trihydroxyborato; sulfido; oxidomethoxy; oxido; trifluoromethyl; and fluoro; and contacting the bisphenol sorbent with an analyte having one or more hydrogen-bond basic groups, where the bisphenol selectively binds with analytes having one or more hydrogen-bond basic groups that circumvent steric groups $R^1$ and $R^2$, forming a bisphenol sorbent-analyte physisorption bond.

In some aspects of the invention, binding with an analyte produces changes in infrared spectral properties that are used as the basis for identifying the bound analyte. The bisphenol sorbent preferentially and selectively binds with stronger hydrogen-bond basic analytes of interest over more weakly-basic interferents.

In other aspects of the invention, a method for collecting an analyte having one or more hydrogen-bond basic groups is provided, which includes providing a bisphenol sorbent having a compound of Formula I or Formula II, wherein $R^1$ and $R^2$ are as described above, and contacting the bisphenol sorbent with a sample including the analyte, wherein the bisphenol selectively binds with the stronger hydrogen-bond basic analyte as compared to weaker hydrogen-bond basic interferents, forming bisphenol sorbent-analyte physisorption bonds.

In still further aspects of the invention, a method for separating a hydrogen-bond basic analyte from a mixture is provided, which includes as a chromatographic stationary phase a bisphenol sorbent comprising a compound of Formula I or Formula II, wherein $R^1$ and $R^2$ are as described above, and contacting the bisphenol sorbent with a sample comprising a hydrogen-bond basic analyte, wherein the bisphenol sorbent selectively binds with hydrogen-bond basic analyte molecules having higher hydrogen-bond basicity over other chemicals having lower hydrogen-bond basicity.

In additional aspects of the invention, a method for forming a polymeric article having a reduced risk of causing endocrine disruption is provided, which includes forming a polymeric article by polymerization of a reaction mixture comprising a bisphenol monomer of Formula A or Formula B, wherein $R^1$ and $R^2$ are as described above. The formed polymeric article comprises free bisphenol monomer of Formula A or Formula B, and wherein upon leaching out of the polymeric article the free bisphenol monomer of Formula A or Formula B causes a reduced level of endocrine disruption as compared to conventional bisphenol monomers that leach out of polymeric articles formed by polymerizing a reaction mixture comprising conventional bisphenol monomers.

Other features and advantages of the present invention will become apparent to those skilled in the art upon examination of the following or upon learning by practice of the invention.

BRIEF DESCRIPTION OF THE DRAWINGS

FIGS. 1A-1F illustrate the problems with existing sorbent molecules, and the solution of the present invention.

In FIG. 1A, the IR spectrum and structure of HCSFA2 are shown.

FIG. 1B illustrates intermolecular bonding of HCSFA2 sorbents between hexafluoroisopropanol functional groups or between a hexafluoroisopropanol group and another sorbent feature.

FIG. 1C illustrates the IR spectrum and hyperbranched structure of HCSFA2.

FIG. 1D illustrates an example of a steric protection of phenolic hydroxyl groups with isopropyl groups, to prevent or reduce intermolecular bonding of sorbent molecules with a bis-phenol architecture.

FIG. 1E outlines the problem to be solved, and the approach taken by the sorbent molecules of the invention.

FIG. 1F illustrates several bisphenol sorbent molecules in accordance with the invention.

FIGS. 2B-2C and FIG. 2A show the infrared spectrum and structure, respectively, of newly developed sorbent 4,4'[2,2,2-trifluoro-1-(trifluoromethyl)ethylidene]bis[2,6-di-tert-butylphenol].

FIGS. 3B-3C and FIG. 3A show the infrared spectrum and structure, respectively, of newly developed sorbent 4,4'-(perfluoropropane-2,2-diyl)bis(2-allyl-6-(tert-pentyl)phenol).

DETAILED DESCRIPTION OF THE INVENTION

Figure 1A:
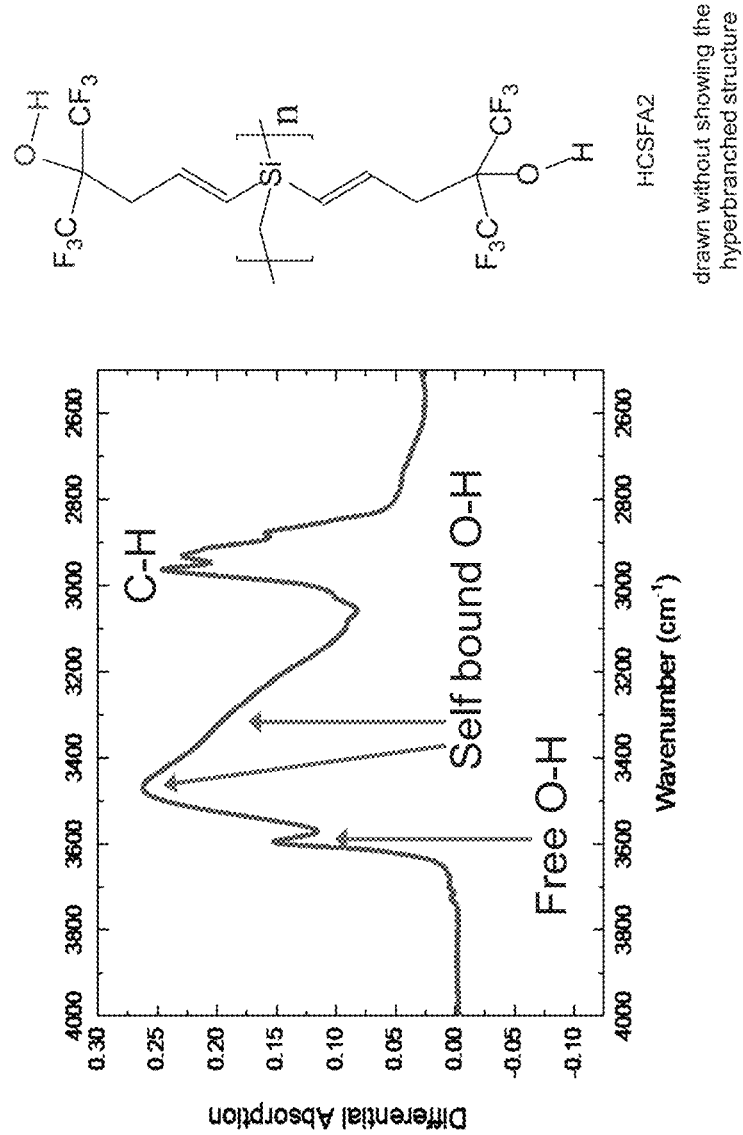

The invention described herein, including the various aspects and/or embodiments thereof, meets the unmet needs of the art, as well as others, by providing strong hydrogen-bond acidic sorbents. The sorbents may be provided in a form that limits or eliminates intra- or inter-molecular bonding of the hydrogen-bond acidic site within a sorbent molecule or between neighboring sorbent molecules, respectively, for example, by providing alkyl steric groups adjacent to the hydrogen-bond acidic site. The hydrogen bond site may be a phenolic structure based on a bisphenol architecture.

The sorbents of the invention may be used in methods for binding to chemicals having hydrogen-bond basic properties, which are present in many toxic or hazardous chemicals. Chemicals that may be bound using the sorbents and methods of the invention include chemical warfare agents (CWAs), toxic industrial chemicals (TICs), and explosives that exhibit hydrogen-bond basic properties, as may be determined by those skilled in the art. These chemicals include, but are not limited to, amines (i.e., TEA (triethylamine)), TPA (tripropylamine), BuAm (butylamine), ammonia), arsines, acetone, acetonitrile, pyridine, DMSO (dimethylsulfoxide), organophosphonates (i.e., DMMP (dimethyl methylphosphonate)), organophosphates (i.e., DIFP (diisopropyl fluorophosphates)), TATP (triacetone triperoxide), and derivatives of phosphonic acid (i.e., the V-series nerve agents, VE (O-ethyl-S[2-(diethylamino)ethyl] ethylphosphonothioate), VG (O,O-diethyl-S[2-(diethylamino)ethyl] phosphorothioate), VM (O-ethyl-S-[2-(diethylamino)ethyl] methylphosphonothioate), and VX (O-ethyl S-(2-diisopropylaminoethyl) methylphosphonothioate)). Explosives that have hydrogen-bond basic properties may also be detected using the sensors, systems, and methods of the invention, including, but not limited to, TNT (2-methyl-1,3,5-trinitrobenzene), TEX (4,10-dinitro-2,6,8,12-tetraoxa-4,10-diazatetracyclo[5.5.0.0$^{5,9}$.0$^{3.11}$]-dodecane), HMX (octahydro-1,3,5,7-tetranitro-1,3,5,7-tetrazocine), CL-20 (2,4,6,8,10,12-Hexanitro-2,4,6,8,10,12-hexaazatetracyclo[5.5.0.0$^{3,11}$.0$^{5,9}$]dodecane), and RDX (1,3,5-trinitro-1,3,5-triazinane), as well as additional explosives as may be determined by those skilled in the art.

The sorbents of the invention may be based on a bisphenol compound, for example, bisphenol A hexafluoride (bisphenol AF, CAS 1478-61-1). The bisphenol compound is ortho- or meta-substituted with one or more steric groups to protect the hydroxyl moieties. Preferably, the steric groups are alkyl groups, and each of the steric groups may be the same or different. These bisphenol sorbents provide strong acidic hydrogen-bond (HB) sites that are protected from self-association or association with other relatively large molecules.

Additional bisphenols suitable for substitution with the steric groups of the invention include, but are not limited to, bisphenol S (CAS 80-09-1), bisphenol C2 (CAS 14868-03-2), bisphenol A (CAS 80-05-7), bisphenol AP (CAS 1571-75-1), bisphenol B (CAS 77-40-7), bisphenol BP (CAS 1844-01-5), bisphenol C (CAS 79-97-0), bisphenol E (CAS 2081-08-5), bisphenol F (CAS 620-92-8), bisphenol G (CAS 127-54-8), bisphenol M (CAS 13595-25-0), bisphenol P (CAS 2167-51-3), bisphenol TMC (CAS 129188-99-4), and bisphenol Z (CAS 843-55-0).

The bisphenol sorbents of the invention preferably comprise a compound of formula A.

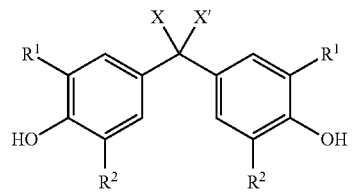

A

X and X' may be selected from hydrogen, methyl, benzyl, trifluoromethyl, ethyl, phenyl, or taken together may form dichloroethene, sulfone, propylbenzene, or an optionally alkyl-substituted cyclic alkyl group such as cyclohexane or 3,3,5-trimethyl cyclohexane. The compounds of formula A include the $R^1$ and $R^2$ substituents in an ortho orientation with respect to the hydroxyl group. In some aspects of the invention, it may be preferable to provide the substituents in the meta position with respect to the hydroxyl group, as shown in formula B.

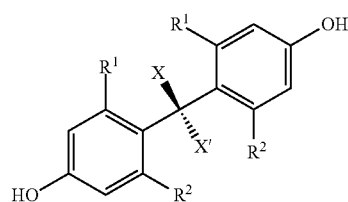

B $R^1$ may be any substituent shown in Table 1 (below), and $R^2$ is either hydrogen (H) or any substituent shown in Table 1 (Remya, G. S. et al., *Phys. Chem. Chem. Phys.* 2016, 18, 20615-20626). By selecting substituents from Table 1, which are relatively bulky but with less inductively electron donating effects than alkyl substituents, it is possible to retain more of the strong hydrogen-bond acidity at the phenolic hydroxyl.

TABLE 1

| Substituent | $\Delta V_C$ | |
|---|---|---|
| $C(Me)=CH_2$ | −0.5 | $S^>$ |
| $CH_2CH_2COOH$ | −0.3 | $S^>$ |
| $Si(Me)(OSiMe_3)_2$ | −0.7 | $S^>$ |
| $OPO(C_3H_7)_2$ | −0.7 | $S^>$ |
| $Si(C_6H_5)Me_2$ | −0.7 | $S^>$ |
| $SiMe_3$ | −0.9 | $S^>$ |
| $CH(OH)C_6H_5$ | −1.0 | $S^>$ |
| $C_6H_4$—4Et | −1.1 | $S^>$ |
| $C_6H_4$—4CHMe$_2$ | −1.2 | $S^>$ |
| $C_6H_4$—4Me | −1.2 | $S^>$ |
| $C_6H_4$—4CMe$_3$ | −1.2 | $S^>$ |
| $N=CHC_6H_5$ | −1.3 | $S^>$ |
| $GeMe_3$ | −1.4 | $S^>$ |
| NHCOMe | −1.4 | $S^>$ |
| $CH(C_6H_5)_2$ | −1.4 | $S^>$ |
| SMe | −1.5 | $S^>$ |
| NMeCOMe | −1.5 | $S^>$ |
| $NHCOC_6H_5$ | −1.5 | $S^>$ |
| $CH_2CH=CH_2$ | −1.6 | $S^>$ |
| $Ge(Et)_3$ | −1.6 | $S^>$ |
| $CH_2C_6H_5$ | −1.8 | $S^>$ |
| NHCOCH(Me)$_2$ | −1.8 | $S^>$ |
| NHCSNHEt | −1.8 | $S^>$ |
| $P(N(Me)_2)_2$ | −1.9 | $S^>$ |
| OH | −2.0 | $S^>$ |
| $C_6H_4$—4OMe | −2.0 | $S^>$ |
| $CH_2PO(OEt)_2$ | −2.0 | $S^>$ |
| SEt | −2.2 | $S^>$ |
| $N(C_6H_5)_2$ | −2.3 | $S^>$ |
| NHCOOMe | −2.4 | $S^>$ |
| Cyclopropyl | −2.4 | $S^>$ |
| $(CH_2)_4NMe_2$ | −2.4 | $S^>$ |
| $CH_2CH_2Si(Me)_3$ | −2.4 | $S^>$ |
| $CH_2PO(C_6H_5)_2$ | −2.5 | $S^>$ |
| $CH_2NMe_2$ | −2.6 | $S^{>>}$ |
| $CH_2C(Me)_3$ | −2.9 | $S^{>>}$ |
| NHCOOEt | −3.0 | $S^{>>}$ |
| $CH_2CH(Me)_2$ | −3.0 | $S^{>>}$ |
| $CH_2CH_2C_6H_3$ | −3.1 | $S^{>>}$ |
| $CH_2CH_2CH_3$ | −3.1 | $S^{>>}$ |
| $(CH_2)_3CH_3$ | −3.2 | $S^{>>}$ |
| CH(Me)(Et) | −3.2 | $S^{>>}$ |
| $NHCOO(CH_2)_3CH_3$ | −3.2 | $S^{>>}$ |
| $(CH_2)_4CH_3$ | −3.2 | $S^{>>}$ |
| $(CH_2)_6CH_3$ | −3.2 | $S^{>>}$ |
| Me | −3.3 | $S^{>>}$ |
| Isopropyl | −3.3 | $S^{>>}$ |
| $NHCOC_6H_4$—4OMe | −3.4 | $S^{>>}$ |
| $CH_2NH_2$ | −3.5 | $S^{>>}$ |
| $NHCONH_2$ | −3.7 | $S^{>>}$ |
| Cyclopentyl | −3.7 | $S^{>>}$ |
| $CH_2C(OH)(Me)_2$ | −3.7 | $S^{>>}$ |
| $N=CHC_6H_4$-4-OMe | −3.8 | $S^{>>}$ |
| Cyclohexyl | −3.8 | $S^{>>}$ |
| $CH_2OH$ | −3.8 | $S^{>>}$ |
| $C(Me)_3$ | −3.9 | $S^{>>}$ |
| Cyclobutyl | −3.9 | $S^{>>}$ |
| $C(Et)_3$ | −4.0 | $S^{>>}$ |
| Et | −4.0 | $S^{>>}$ |
| $C(Et)(Me)_2$ | −4.2 | $S^{>>}$ |
| $OSiMe_3$ | −4.2 | $S^{>>}$ |
| $OCH_2CH=CH_2$ | −4.8 | $S^{>>}$ |
| $NHC_6H_5$ | −4.8 | $S^{>>}$ |
| $CH_2OSi(CH_3)_3$ | −4.8 | $S^{>>}$ |
| $CH_2Si(Me)_3$ | −4.9 | $S^{>>}$ |
| OMe | −5.0 | $S^{>>}$ |
| NHOH | −5.1 | $S^{>>}$ |
| $N=NNMe_2$ | −5.6 | $S^{>>}$ |
| $OCH_2CH_3$ | −5.8 | $S^{>>}$ |
| NHCONHEt | −5.8 | $S^{>>}$ |
| $O(CH_2)_3CH_3$ | −5.9 | $S^{>>}$ |

TABLE 1-continued

| Substituent | $\Delta V_C$ | |
|---|---|---|
| $OCH_2CH_2CH_3$ | −6.0 | $S^{>>}$ |
| $NHPO(C_3H_7)_2$ | −6.2 | $S^{>>}$ |
| $O(CH_2)_4CH_3$ | −6.2 | $S^{>>}$ |
| $OCHMe_2$ | −6.5 | $S^{>>}$ |
| $N=C(Me)NHC_6H_5$ | −6.6 | $S^{>>}$ |
| $NH_2$ | −9.0 | $S^{>>>}$ |
| NHMe | −11.2 | $S^{>>>}$ |
| $NHNH_2$ | −11.2 | $S^{>>>}$ |
| NHEt | −11.4 | $S^{>>>}$ |
| $NH(CH_2)_3CH_3$ | −11.6 | $S^{>>>}$ |
| $N(Et)_2$ | −11.9 | $S^{>>>}$ |
| $N(Me)_2$ | −12.3 | $S^{>>>}$ |
| $N(C_3H_7)_2$ | −12.9 | $S^{>>>}$ |
| $CF_2OCF_2^-$ | −57.6 | $S^{>>>>}$ |
| $OCH_2CH_2CH_2O^-$ | −63.2 | $S^{>>>>}$ |
| $OCH_2CH_2O^-$ | −66.8 | $S^{>>>>}$ |
| $SO_3^-$ | −67.2 | $S^{>>>>}$ |
| $PO_3H^-$ | −70.4 | $S^{>>>>}$ |
| $SO_2^-$ | −73.2 | $S^{>>>>}$ |
| $CH_2CO_2^-$ | −74.5 | $S^{>>>>}$ |
| $CO_2^-$ | −77.5 | $S^{>>>>}$ |
| $OPO_3H^-$ | −77.8 | $S^{>>>>}$ |
| $CH_2CH_2CH_2^-$ | −83.2 | $S^{>>>>}$ |
| $NNO_2^-$ | −83.7 | $S^{>>>>}$ |
| $B(OH)_3^-$ | −88.9 | $S^{>>>>}$ |
| $S^-$ | −95.8 | $S^{>>>>}$ |
| $OCH_2O^-$ | −102.6 | $S^{>>>>}$ |
| $O^-$ | −113.4 | $S^{>>>>}$ |

The invention further relates to bisphenols of formula I and formula II,

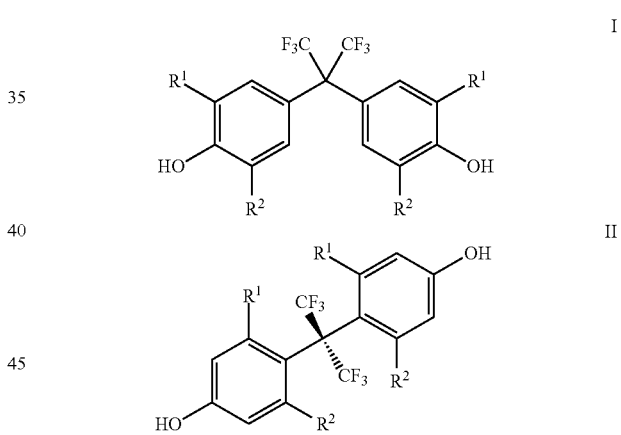

where $R^1$ is a substituent selected from prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl(methyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl;

(4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenylamino; ((trimethylsilyl)oxy)methyl; (trimethylsilyl)methyl; methoxy; hydroxyamino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy) 2; carboxylate; (hydroxyoxidophosphoryl)oxy; propan-1-id-3-yl; nitroamido; trihydroxyborato; sulfido; oxidomethoxy; oxido; trifluoromethyl; and fluoro.

$R^2$ is hydrogen or a substituent selected from prop-1-en-2-yl; 2-carboxyethyl; 1,1,1,3,5,5,5-heptamethyltrisiloxan-3-yl; (dipropylphosphoryl)oxy; dimethyl(phenyl)silyl; trimethylsilyl; hydroxy(phenyl)methyl; 4-ethylphenyl; 4-isopropylphenyl; 4-methylphenyl; 4-(tert-butyl)phenyl; benzylideneamino; trimethylgermyl; acetylamino; diphenylmethyl; methylthio; acetyl (methyl)amino; benzoylamino; 2-propenyl; prop-2-enyl; triethylgermyl; benzyl; isobutyramido; (ethylcarbamothioyl)amino; bis(dimethylamino)phosphaneyl; hydroxy; 4-methoxyphenyl; (diethoxyphosphoryl)methyl; ethylthio; diphenylamino; (methoxycarbonyl)amino; cyclopropyl; 4-(dimethylamino)butyl; 2-(trimethylsilyl)ethyl; (diphenylphosphoryl)methyl; (dimethylamino)methyl; 2,2-dimethylpropyl; (ethoxycarbonyl)amino; 2-methylpropyl; phenylethyl; propyl; butyl; sec-butyl; (butoxycarbonyl)amino; pentyl; heptyl; methyl; propan-2-yl; (4-methoxybenzoyl)amino; aminomethyl; carbamoylamino; cyclopentyl; 2-hydroxy-2-methylpropyl; (4-methoxybenzylidene)amino; cyclohexyl; hydroxymethyl; tert-butyl; cyclobutyl; 3-ethylpentan-3-yl; ethyl; 1,1-dimethylpropyl; (trimethylsilyl)oxy; prop-2-enoxy; phenylamino; ((trimethylsilyl)oxy)methyl; (trimethylsilyl)methyl; methoxy; hydroxyamino; 3,3-dimethyltriaz-1-en-1-yl; ethoxy; ethylcarbamoylamino; butoxy; propoxy; (dipropylphosphoryl)amino; pentyloxy; propan-2-yloxy; (1-(phenylamino)ethylidene)amino; amino; methylamino; hydrazinyl; ethylamino; butylamino; diethylamino; dimethylamino; dipropylamino; ((difluoromethaneidyl)oxy)difluoromethyl; 3-oxidopropoxy; 2-oxidoethoxy; sulfonato; hydroxyoxidophosphoryl; sulfinato; 2-(carboxylatomethy) 1; carboxylate; (hydroxyoxidophosphoryl)oxy; propan-1-id-3-yl; nitroamido; trihydroxyborato; sulfido; oxidomethoxy; oxido; trifluoromethyl; and fluoro.

The invention additionally relates to di-substituted bisphenols, where $R^1$ is a substituent selected from the substituents above (other than hydrogen), and $R^2$ is hydrogen. Such di-substituted bisphenols are named 4,4'-(perfluoropropane-2,2-diyl)bis(2-(substituent)phenol).

The invention also relates to tetra-substituted bisphenols where $R^1$ and $R^2$ are the same substituent, and are selected from the substituents above (other than hydrogen). Such tetra-substituted bisphenols are named 4,4'-(perfluoropropane-2,2-diyl)bis(2,6-di(substituent)phenol).

The invention further relates to tetra-substituted bisphenols where $R^1$ and $R^2$ are different substituents selected from the substituents above (neither is hydrogen). Such tetra-substituted bisphenols are named 4,4'-(perfluoropropane-2,2-diyl)bis(3-(first substituent)-5-(second substituent)phenol).

The invention additionally relates to di-substituted bisphenols, where $R^1$ is a substituent selected from the substituents above (other than hydrogen), and $R^2$ is hydrogen. Such di-substituted bisphenols are named 4,4'-(perfluoropropane-2,2-diyl)bis(3-(substituent)phenol).

The invention also relates to tetra-substituted bisphenols where $R^1$ and $R^2$ are the same substituent, and are selected from the substituents above (other than hydrogen). Such tetra-substituted bisphenols are named 4,4'-(perfluoropropane-2,2-diyl)bis(3,5-di(substituent)phenol).

The invention further relates to tetra-substituted bisphenols where $R^1$ and $R^2$ are different substituents, and are selected from the substituents above (other than hydrogen). Such tetra-substituted bisphenols are named 4,4'-(perfluoropropane-2,2-diyl)bis(3-(first substituent)-5-(second substituent)phenol).

The invention additionally relates to combinations of two or more of the bisphenol sorbents of the invention together in an admixture to effect a change in the solid physical properties of one bisphenol with a liquid like bisphenol.

In this invention, one or more acidic hydrogen-bond (HB) sites in the sorbent molecule are protected by an ortho- or meta-substituted phenolic structure. Preferably at least half of the HB sites in the sorbent molecule are present in the free hydroxyl form at any one time. More preferably, about 75% of the HB sites in the molecule are present in the free hydroxyl form. According to some presently-preferred aspects, greater than 95% of the HB sites in the sorbent molecule are present in the free hydroxyl form. To prevent intermolecular bonding between the hydrogen-bond acidic sites and neighboring sorbent molecules, alkyl steric groups may be provided in different positions neighboring the HB acid site to limit or eliminate the approach of relatively large molecules, such as the sorbent itself. By synthesizing and testing various alkylated phenolic structures, the invention has identified how large the alkylated structures need to be to successfully prevent the undesirable intermolecular bonding between the hydrogen-bond acidic sites and neighboring sorbent molecules. When $R^1$ and/or $R^2$ is methyl (1C), ethyl (2C), and propyl (3C), the substituents may not provide enough steric hindrance to prevent intermolecular hydrogen bonding between bisphenol type sorbent molecules. As the steric groups increase in both size and amount of branching, the amount of free hydroxyl increases. In one aspect of the invention, a bisphenol sorbent where $R^1$=propyl and $R^2$=1,1-dimethylpropyl is preferred. This sorbent maximizes the amount of free hydroxyl and also presents in an ideal physical state, a viscous oil, to allow rapid analyte uptake.

Additional preferred bisphenol sorbents in accordance with the invention include 4,4'-(perfluoropropane-2,2-diyl)bis(2-propylphenol), 4,4'-(perfluoropropane-2,2-diyl)bis(2,6-di-tert-butylphenol), 4,4'-(perfluoropropane-2,2-diyl)bis(2-(tert-pentyl)phenol), 4,4'-(perfluoropropane-2,2-diyl)bis(2-(tert-pentyl)-6-propylphenol), 4,4'-(perfluoropropane-2,2-diyl)bis(2,6-dipropylphenol), 4,4'-(perfluoropropane-2,2-diyl)bis(2,6-dimethylphenol), 4,4'-(perfluoropropane-2,2-diyl)bis(2,6-diethylphenol), 4,4'-(perfluoropropane-2,2-diyl)bis(2-ethyl-6-(tert-pentyl)phenol), 4,4'-(perfluoropropane-2,2-diyl)bis(2,6-di-tert-pentylphenol), 4,4'-(perfluoropropane-2,2-diyl)bis(2-isopropyl-6-(tert-pentyl)phenol), 4,4'-(perfluoropropane-2,2-diyl)bis(2-ethylphenol), and 4,4'-(perfluoropropane-2,2-diyl)bis(2,6-bis(trimethylsilyl)phenol).

Figure 1B:
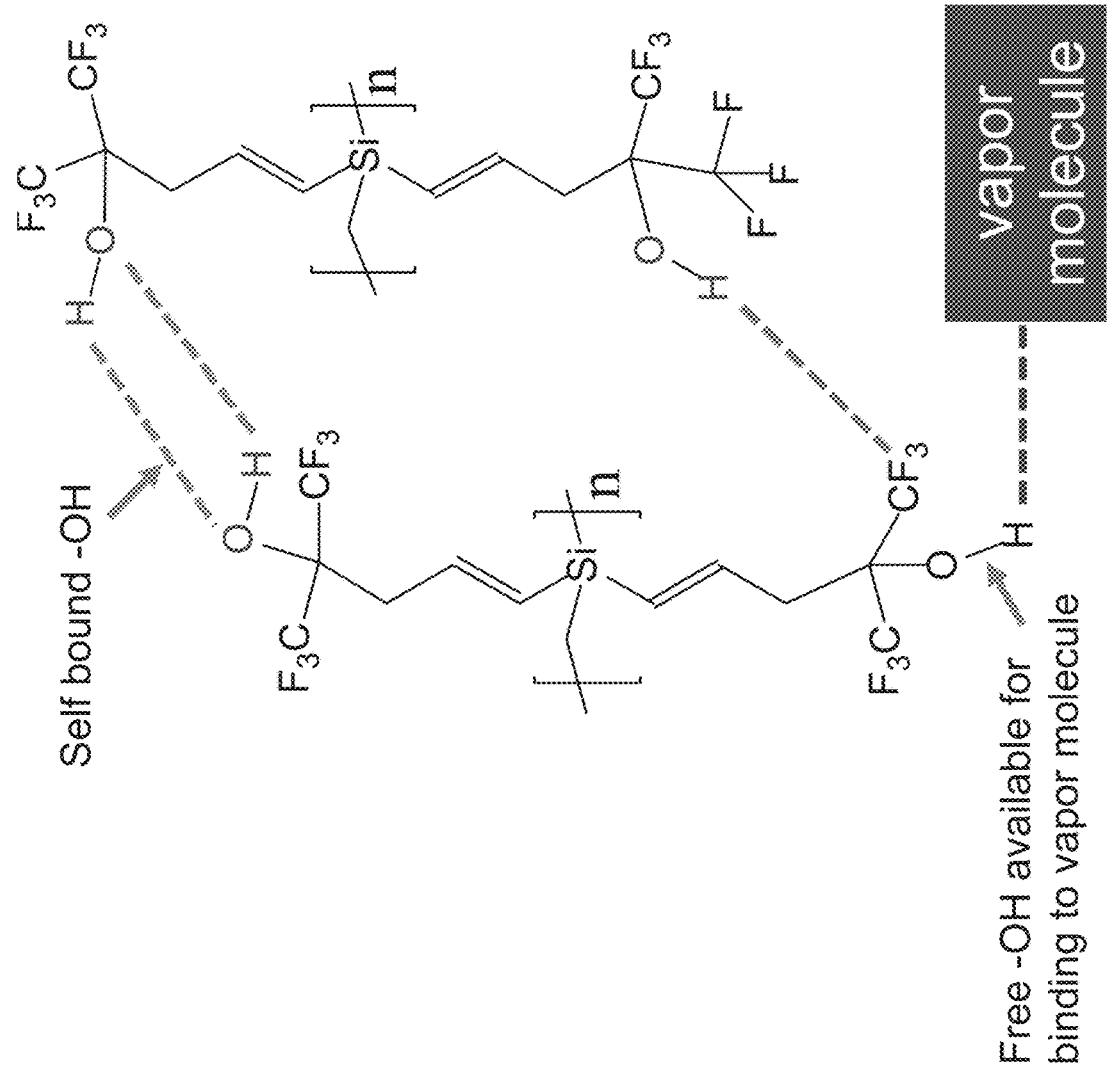

In order to illustrate the problems associated with existing bisphenol sorbents, FIG. 1A provides the infrared spectrum and structure of known sorbent HCSFA2. As evidenced by the infrared spectrum, this sorbent suffers from a high degree of self-association, which unfavorably binds and ties up the hydroxyl (—OH) and reduces the efficacy of analyte binding. FIG. 1B further illustrates the intermolecular bonding of HCSFA2 sorbents between hexafluoroisopropanol functional groups. FIG. 1C depicts the infrared spectrum and hyperbranched structure of HCSFA2. As evidenced by the infrared spectrum, this sorbent has been found to suffer from a high degree of self-association, which unfavorably binds the hydroxyl (—OH) and reduces the efficacy of analyte binding. Typically, in sorbents with hydroxyl functionality, less than 10% of the hydroxyl is in the free state at any moment in time.

Figure 1D:
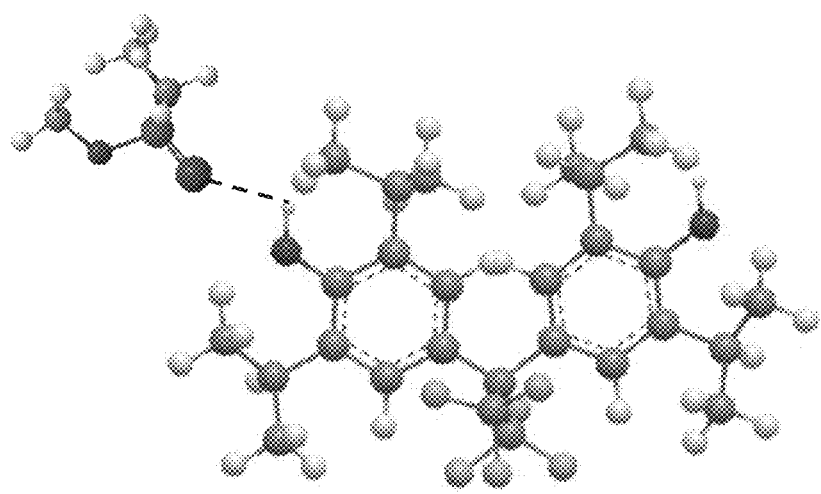
Figure 1D:
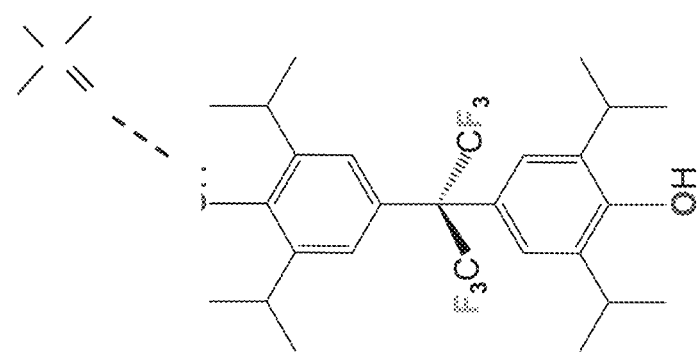

In contrast, FIG. 1D shows a sterically-hindered phenolic structure in accordance with the invention that mitigates or prevents the intermolecular bonding challenge for sorbents with hexafluoroisopropanol functional groups. The alkyl groups form a vapor binding pocket, but hinder the approach of neighboring and relatively large sorbent molecules. The steric groups also reduce crystal formation, which causes the sorbents to take the form of a viscous oil, which is desirable for sorbing analyte in analytical and trapping or protection applications. A 3D model showing the steric group of the invention is also included in FIG. 1D.

Figure 1E:
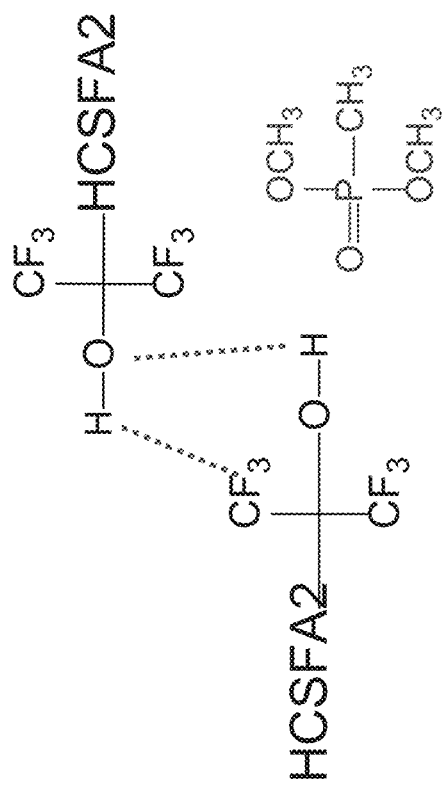
Figure 1E:
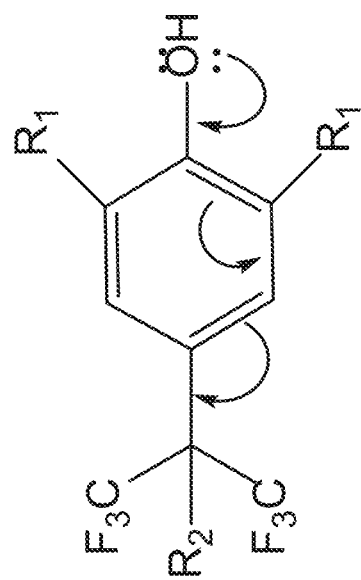

FIG. 1E outlines a strategy to eliminate or reduce sorbent self-bound —OH interactions in accordance with the invention. The challenge is that existing sorbents have —OH tied up with adjacent —OH and —CF$_3$ groups (upper structure), which reduces vapor bonding opportunities for the neighboring DMMP molecule. By separating the —OH and CF$_3$ groups using a conjugated phenolic system (lower structure), the invention is able to limit sorbent-sorbent intermolecular self-bonding, and the —OH molecules are therefore more readily available to bind with chemicals of interest.

Figure 1F:
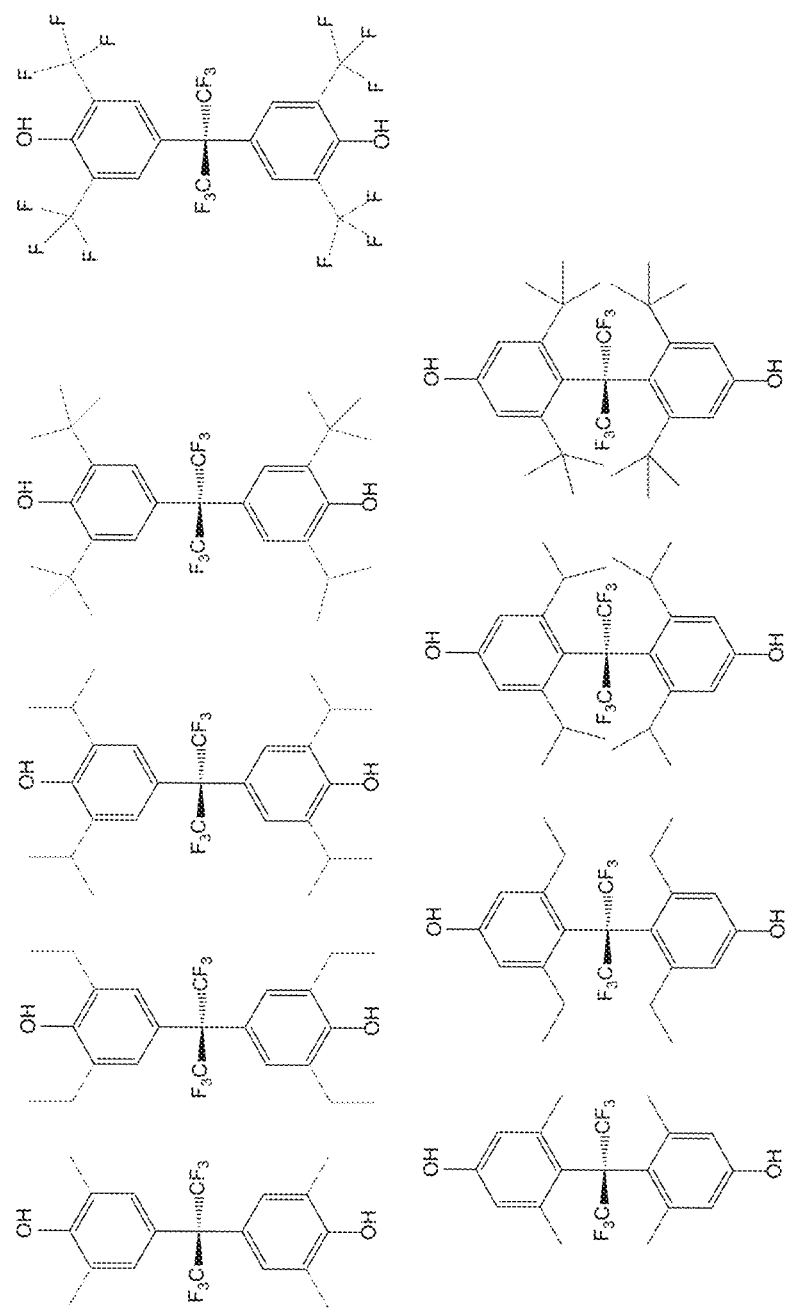
Figure 1G:
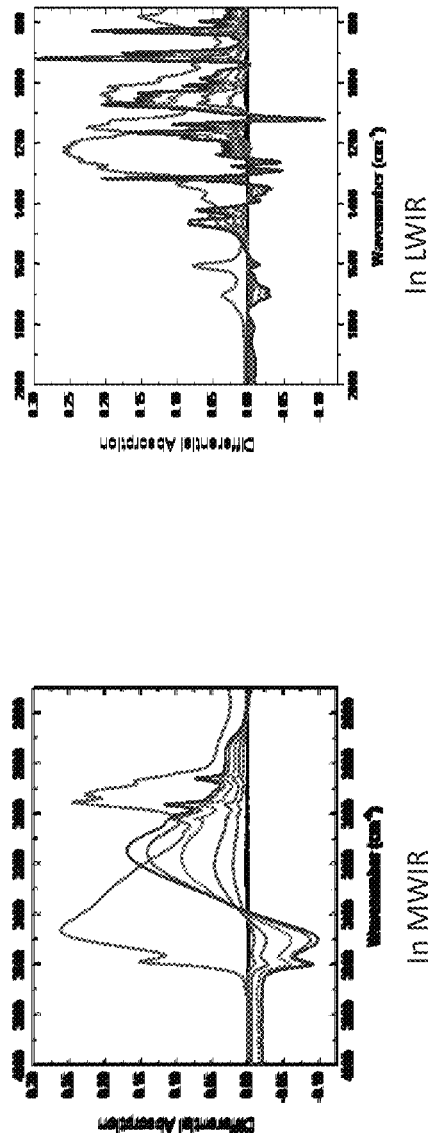
FIG. 1G provides vapor-sorbent ATR-IR differential spectra for the sorbent HCSFA2 at different concentrations of DMMP, illustrating the spectral changes in the MWIR and LWIR, providing the basis of an IR sensing path to detecting a chemical of interest.

FIG. 1G illustrates HCSFA2 sorbent-DMMP IR solutochromic spectra data sets, showing differential absorption for DMMP concentrations ranging from 3.9 ppm to 0.0 ppm, as well as HCSFA2 polymer absorption. The contributions to spectral changes with vapor exposure for: 1) Vapor-sorbent interaction sites; 2) Separation of sorbent-sorbent molecule interactions; and 3) Vapor present in the sorbent are shown.

The bisphenol sorbents of the invention are designed to sterically shield the phenolic hydroxyl (hydrogen-bond acidic site) from undesired interactions with other sorbent molecules, leaving an exclusive pocket available for the analytes of interest. The availability of more sorbent-analyte binding sites allows binding to more analyte molecules per unit time in the sorbent, from the contacted phase laden with analyte, leading to superior hypersorbents than the current standards. The analyte laden phase maybe a gaseous atmosphere or a condensed phase. In addition, the bulkier alkyl groups ortho-substituted to the phenolic hydroxyl lead to more liquid-like properties than crystalline properties, which is a desirable characteristic for these types of sorbents.

In general, the sorbents provide a means to concentrate or trap hazardous chemicals or explosives (analytes) to the sorbent phase. The concentration of analyte into the sorbent phase can be augmented by several orders of magnitude higher than that in the ambient air or the condensed phase laden with analyte, enabling effective analyte sampling for trapping or trace detection of chemicals. These sorbents are designed to have extreme hydrogen-bond acidic properties, activated by fluorine chemistries, to target the complementary hydrogen-bond basic properties of the analytes of interest. These molecular interactions are based on reversible physisorption-type processes, allowing these sorbents to be reused multiple times. At thicker coating levels, the sorbent can act to trap chemicals for extended time periods at ambient temperatures, and provides a means to effectively remove chemicals from air or condensed phases to clean air or water for protection or filtration type applications.

In some aspects of the invention, if the bisphenol sorbent is a crystalline solid, the sorbent may be dispersed or dissolved into a liquid or resin-like host material, which mitigates the challenge of slow chemical diffusion into the crystalline bisphenol sorbent. Suitable host materials may include, but are not limited to 4,4'-(perfluoropropane-2,2-diyl)bis(2-(tert-pentyl)-6-propylallyl-6-(tert-pentyl)phenol), poly(dimethylsiloxane), (PDMS), poly(methylphenylsiloxane), and poly(dimethylsiloxane-co-methylphenylsiloxane).

FIGS. 6A-6D show synthetic schemes for producing the various bisphenols of the invention, as well as an overview of the structures of presently-preferred bisphenols in accordance with the invention. Schemes 1-5 describe synthetic routes to sorbents that have been synthesized and characterized. Schemes 6-9 describe planned synthetic routes for additional sorbent candidates. Scheme 10 shows a summary of the structures of presently-preferred bisphenol sorbents that may be synthesized in accordance with the invention.

Figure 6A:
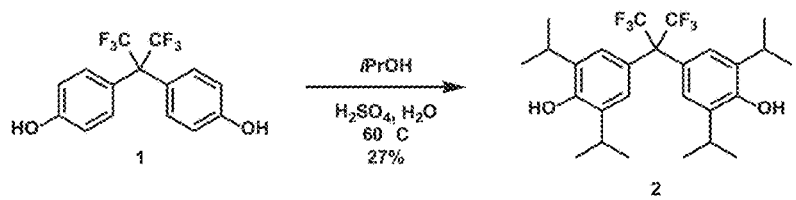
FIGS. 6A-6D show synthetic schemes for bisphenols of the invention, and a summary of the bisphenol sorbents.
Figure 6A:
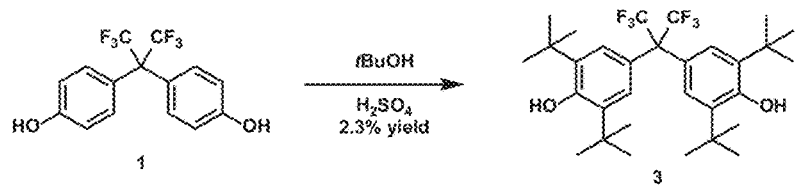
Figure 6A:
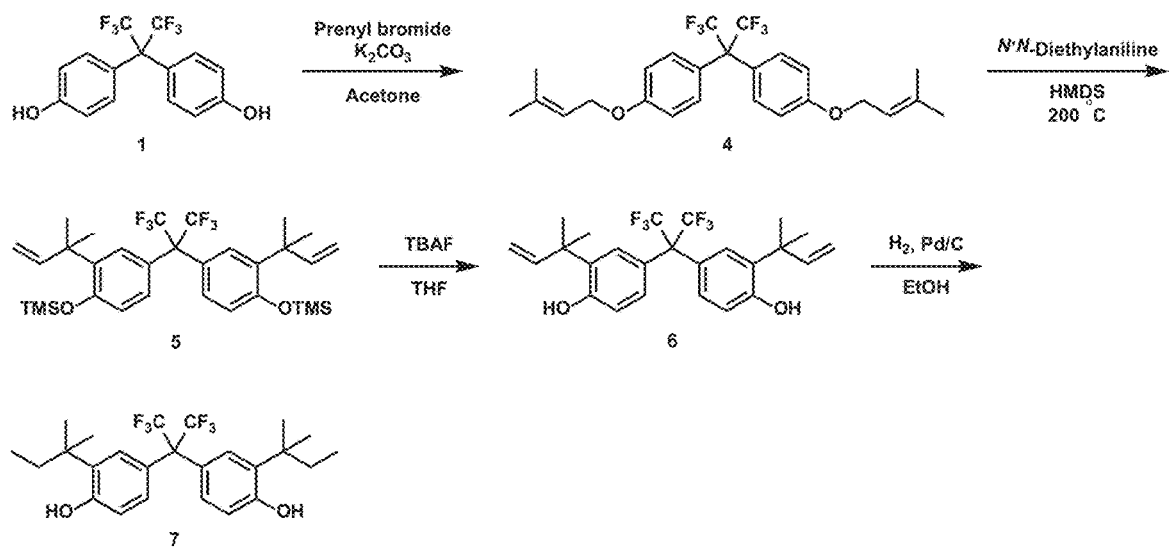
Figure 6B:
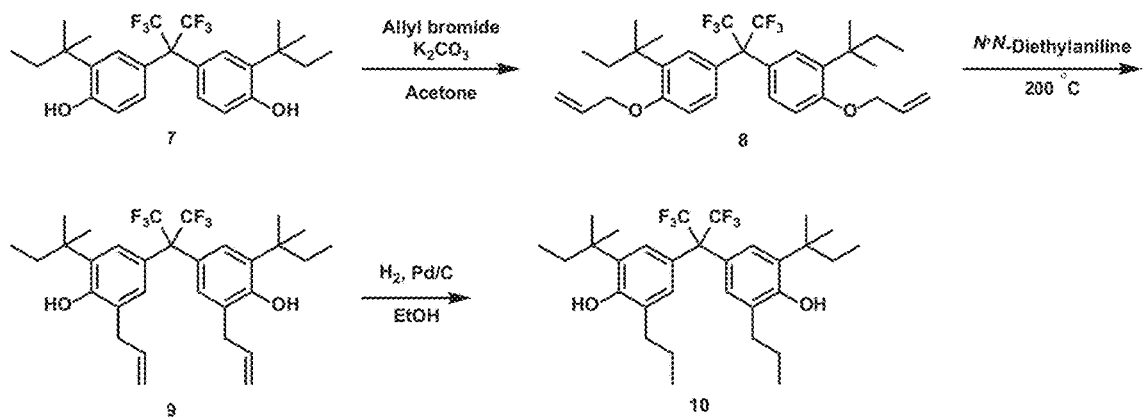
Figure 6B:
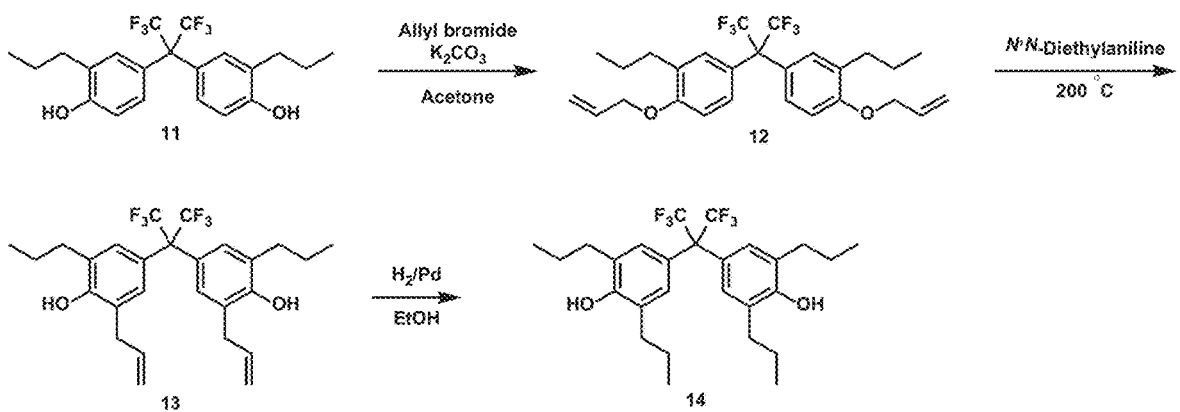
Figure 6B:
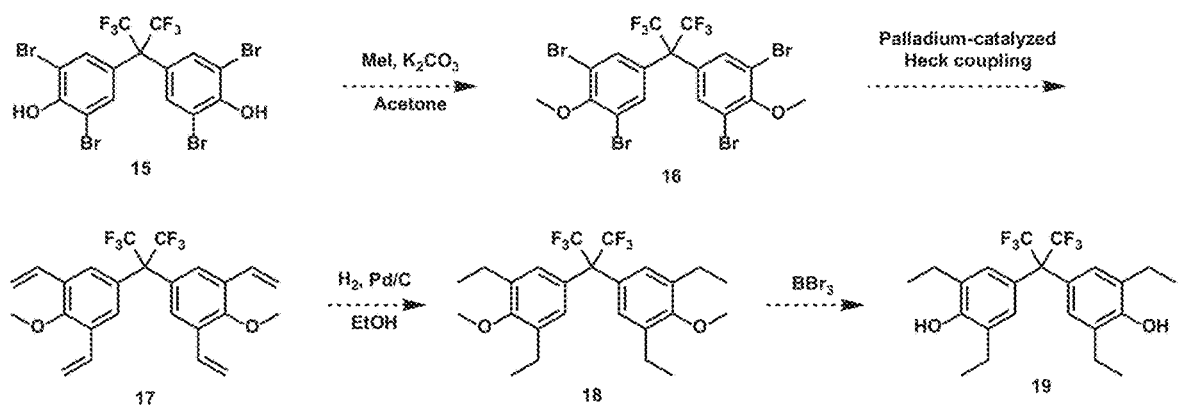
Figure 6C:
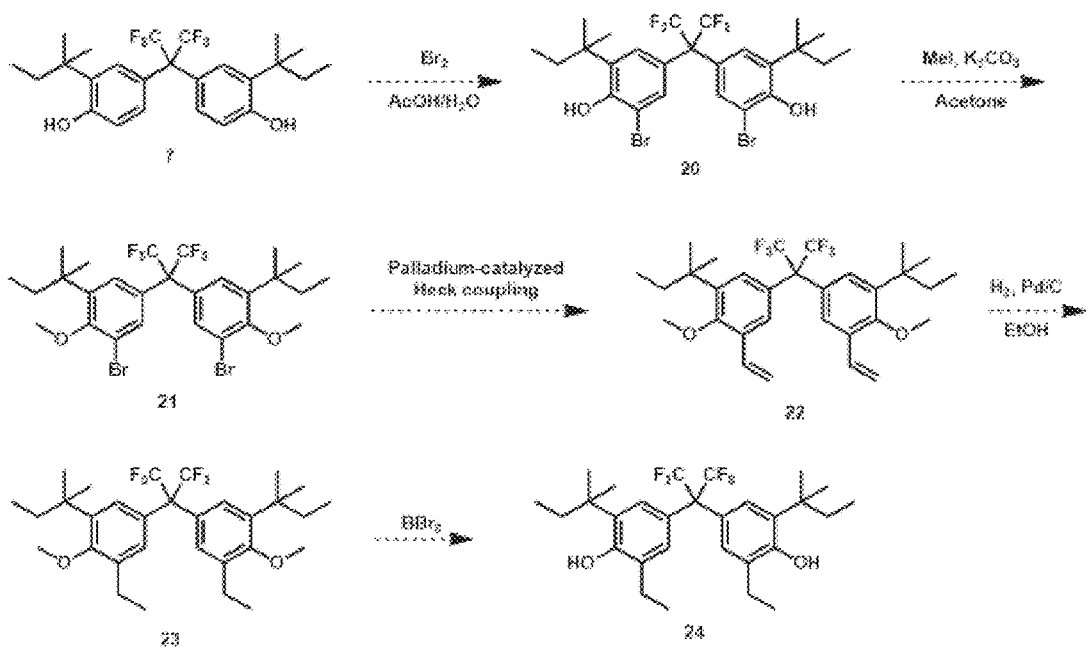
Figure 6C:
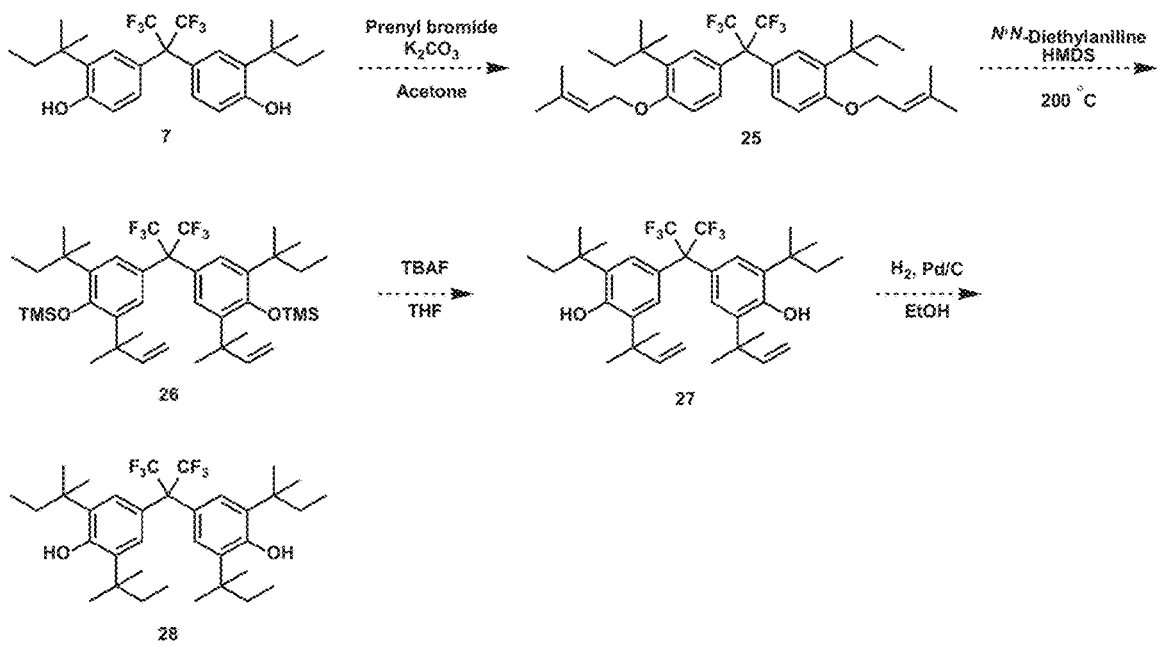
Figure 6D:
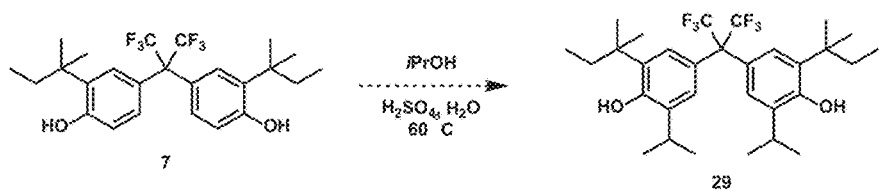
Figure 6D:
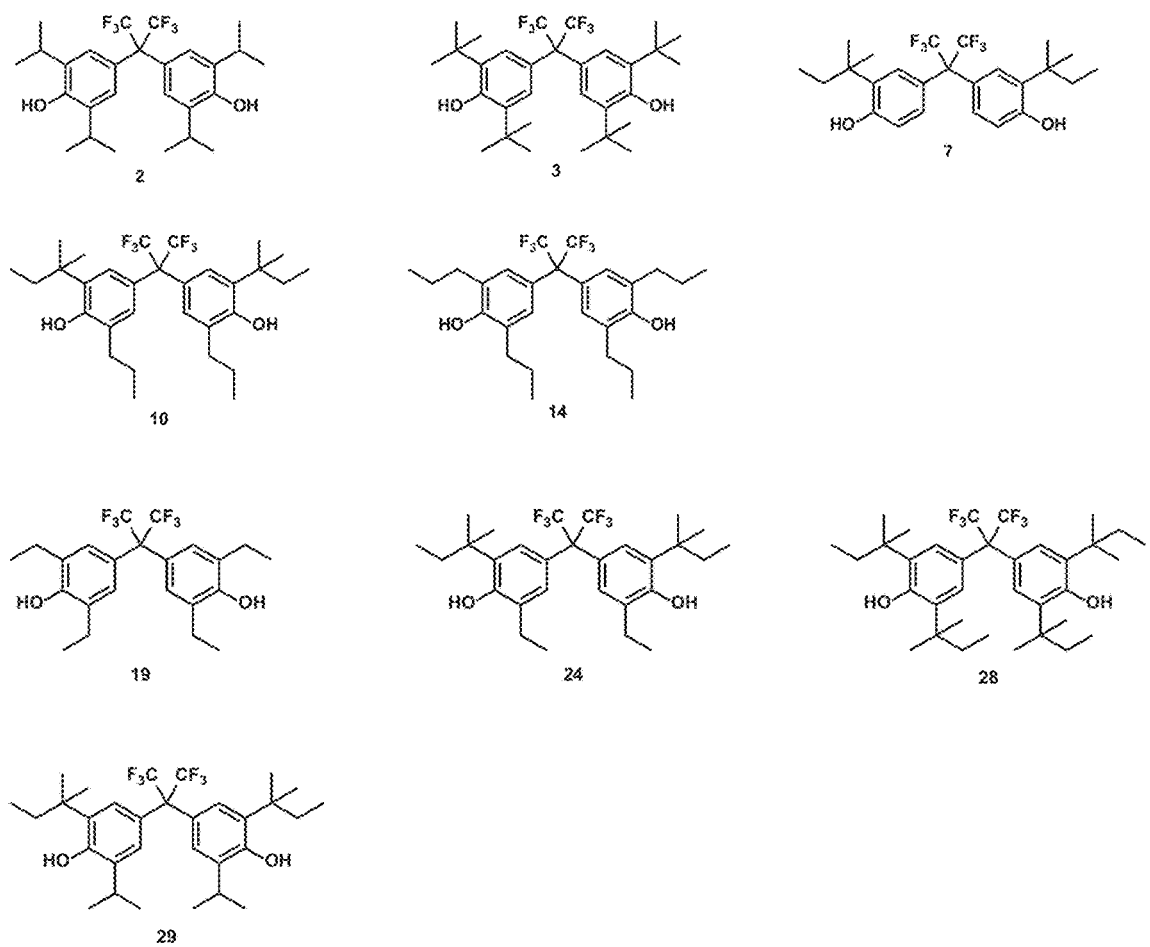

FIGS. 1F and 6D illustrate several presently-preferred bisphenol sorbent molecules in accordance with the invention.

Of the newly-developed sorbents tested, 4,4'-[2,2,2-trifluoro-1-(trifluoromethyl)ethylidene]bis[2,6-di-tert-butylphenol] 3 shows the greatest amount of free hydroxyl, as evidenced by infrared spectroscopy. There is almost solely free hydroxyl present. FIGS. 2B-2C and FIG. 2A show the infrared spectrum and structure, respectively, of 4,4'-[2,2,2-trifluoro-1-(trifluoromethyl)ethylidene]bis[2,6-di-tert-butylphenol] 3. As evidenced by the infrared spectrum, this sorbent shows little evidence of self-association, which is an ideal property for the sorbents of the invention. However, this bisphenol is a powdery solid, which is not the ideal physical state for sorption of analyte molecules in analytical, trapping or protection applications.

The newly developed sorbent 4,4'-(perfluoropropane-2,2-diyl)bis(2-(tert-pentyl)-6-propylphenol) 10 also shows mostly free hydroxyl in the infrared spectrum, with a small amount of self-association evident. FIGS. 3B-3C and FIG. 3A show the infrared spectrum and structure, respectively, of 4,4'-(perfluoropropane-2,2-diyl)bis(2-(tert-pentyl)-6-propylphenol) 10. This sorbent is a viscous oil, which is the ideal physical state. This sorbent is a viscous oil, which is the ideal physical state.

Figure 4:
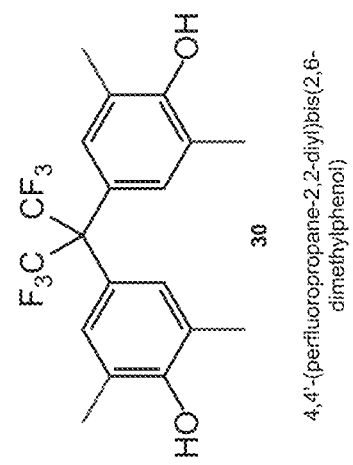
FIG. 4 shows the infrared spectrum and structure of known sorbent 4,4'-(perfluoropropane-2,2-diyl)bis(2,6-dimethylphenol).
Figure 4:
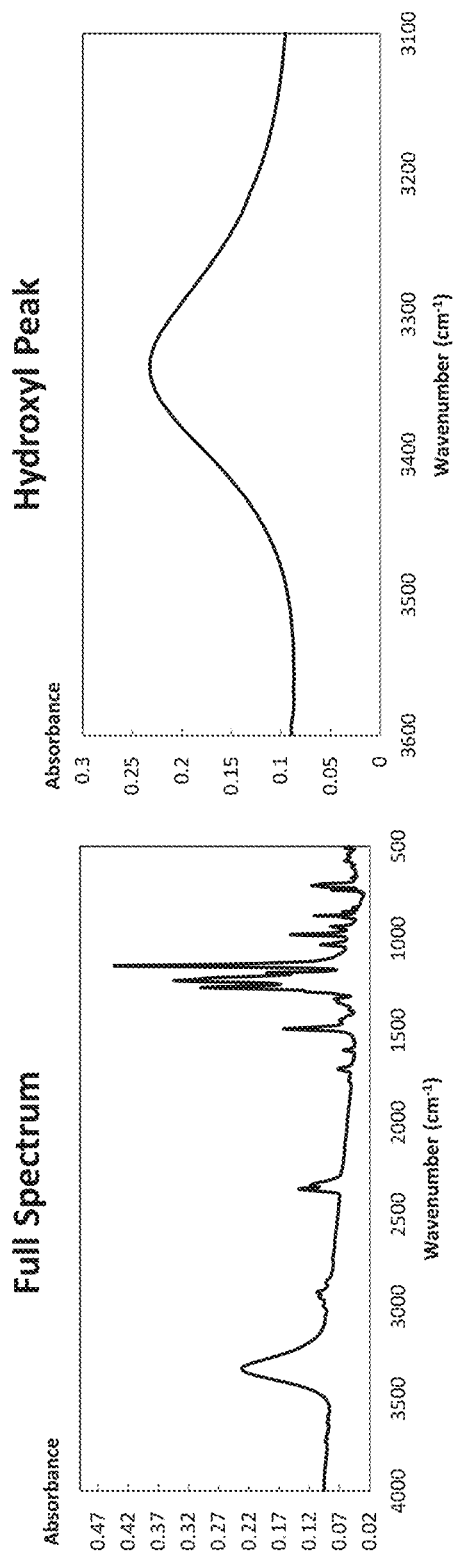

In comparison, known compound 4,4'-(perfluoropropane-2,2-diyl)bis(2,6-dimethylphenol) 30 was also synthesized to show the effect of the alkyl substituent on the degree of self-association (see, e.g., FIG. 4; Dai, Y., et al., *Macromolecules* 2004, 37, 1403-1410). The infrared spectrum and structure of known sorbent compound 4,4'-(perfluoropropane-2,2-diyl)bis(2,6-dimethylphenol) 30 are shown in FIG. 4. As evidenced by the infrared spectrum, this sorbent suffers from a high degree of self-association, with no free hydroxyl visible.

Figure 5:
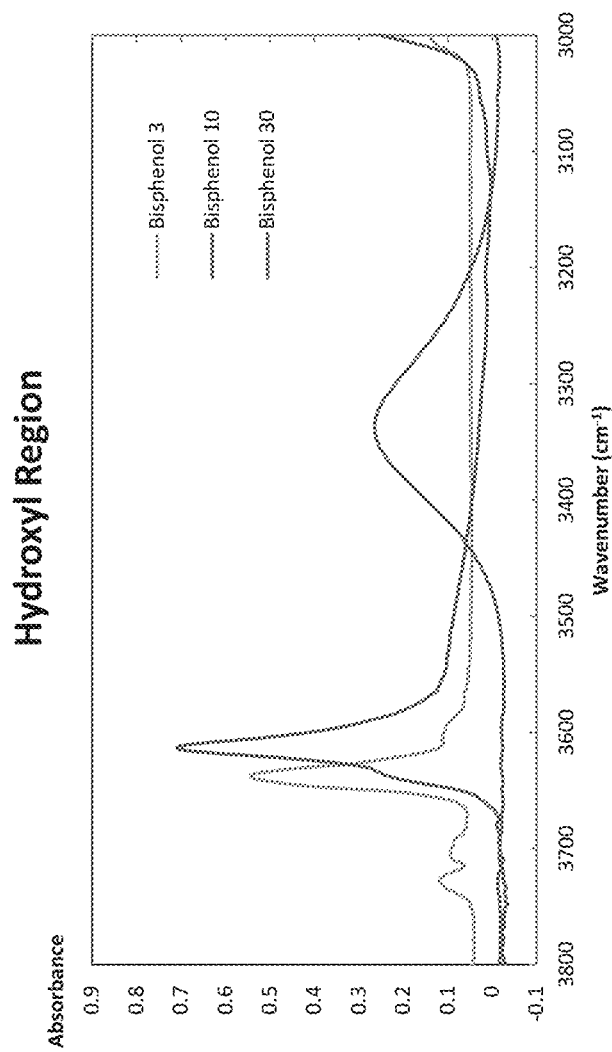
FIG. 5 shows an overlay of the IR spectra of bisphenols 3, 10, and 30.

An overlay of the hydroxyl peaks of the infrared spectra of bisphenols 3, 10, and 30 is shown in FIG. 5. Bisphenol 30, with methyl groups ortho-substituted to the hydroxyls, shows the greatest degree of self-association. Bisphenols 3 and 10, substituted with bulkier alkyl substituents ortho- to the hydroxyls, have substantially more free hydroxyl evident and less self-association. In FIG. 5 the absorbance values (y-axis) are normalized for comparison. Wavenumbers (x-axis, representing the IR shifts) have not been modified.

The sorbents of the invention are typically applied to a substrate as a thin film. For gas sensing applications, this typically includes coatings measured in 10's of nanometers of thickness. For collection or protection applications, this typically includes coatings measured in 100's of nanometers to micrometers of thickness. The coatings can be applied to any solid substrate, e.g., flat substrates, porous substrates or dense particles. The sorbents of the invention may also be functionalized to provide reactive sites (e.g. alkenic structures), for grafting to solid substrates, attaching to a polymer backbone as pendent groups, or splicing into and as part of a polymer backbone. The latter has been performed with other bisphenol structures (e.g., BSP3), as described in U.S. Pat. No. 6,015,869 to Grate, J. W. et al.

The bisphenol sorbents of the invention may be provided as a layer or coating, such as by immobilizing on a surface of a support structure, or within pores contained within a porous support structure. Support structures suitable for use as supports for the bisphenol sorbents of the invention include, but are not limited to, silicon, carbon, and polymers. Examples include metalorganic frameworks (MOFs), zeolites, CARBOTRAP® adsorbent, CARBOPACK™ adsorbent, activated coconut charcoal, HAYESEP® porous polymer adsorbent, CARBOXEN® adsorbent, CARBOSIEVE® adsorbent, GRAPHSPHERE™ adsorbent, FLORISIL® adsorbent, AMBERLITE® adsorbents, and diatomaceous earth. The bisphenol sorbents of the invention may also be coated as a chromatographic stationary phase. The invention is not to be considered limited to use with any particular support structures, which may differ depending on the particular application for which the bisphenol sorbents are used. The invention further relates to support structures having the bisphenol sorbents of the invention sorbed thereto, as well as to chromatography stationary phases having the bisphenol sorbents as the stationary phase.

By adjusting the thickness of the sorbent layer or coating on or within a support structure, enhanced retention of the analyte may be conferred such that collection of analyte over a period of exposure time can be achieved. Subsequent heating of the trapped analyte allows its release for regeneration of the sorbent or subsequent analytical operations.

By immobilization of the sorbent to a solid substrate or by fixing it to the substrate, or by incorporating it into a porous framework, this opens up applications to sample analyte from condensed phases such as water. One example of a commercial device that may be used in accordance with this aspect of the invention is a Solid Phase MicroExtraction (SPME) device. The sorbents described in this invention will find utility as coatings for SPME or related devices for air or condensed phase applications.

These sorbents can also be used for advanced sensing, trapping, protection, and analytical applications. Examples of such applications include collection, preconcentrator, gas chromatography stationary phases, sensing, microsensor coating applications, and coatings for porous support structure or nanoparticulate materials, gas mask cartridges or other types of air filter cartridges.

Figure 7:
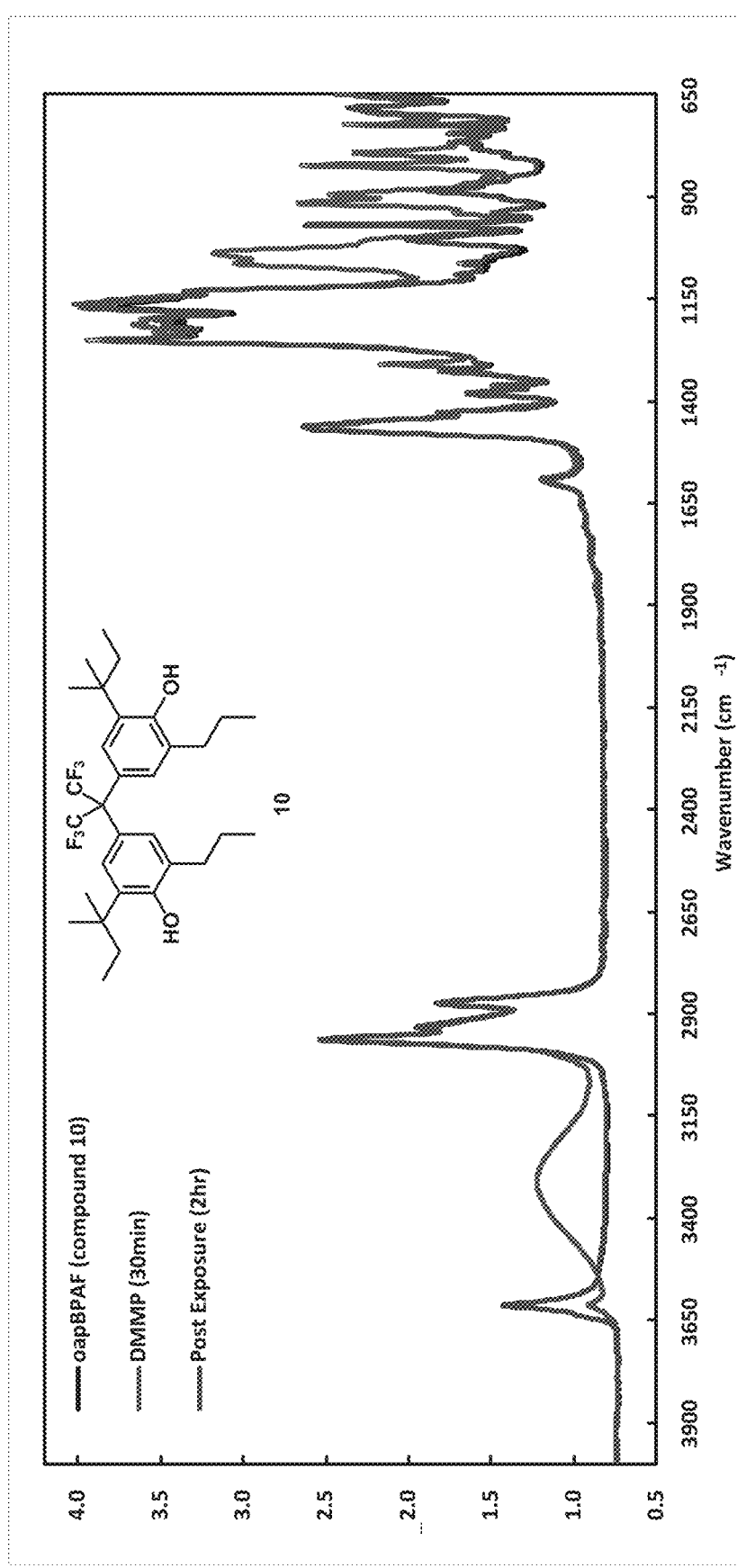
FIG. 7 shows IR spectra for vapor-sorbent binding data for the bisphenol 10 sorbent exposed to an example vapor.
Figure 9:
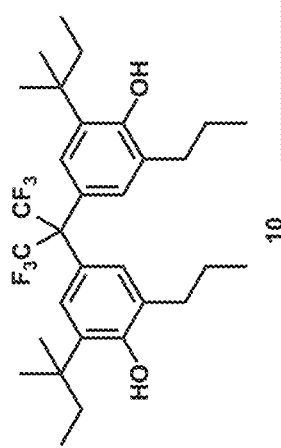
FIG. 9 shows the response of a QCM sensor coated with bisphenol 10 to DMMP vapor at a concentration of 1 ppm.
Figure 9:
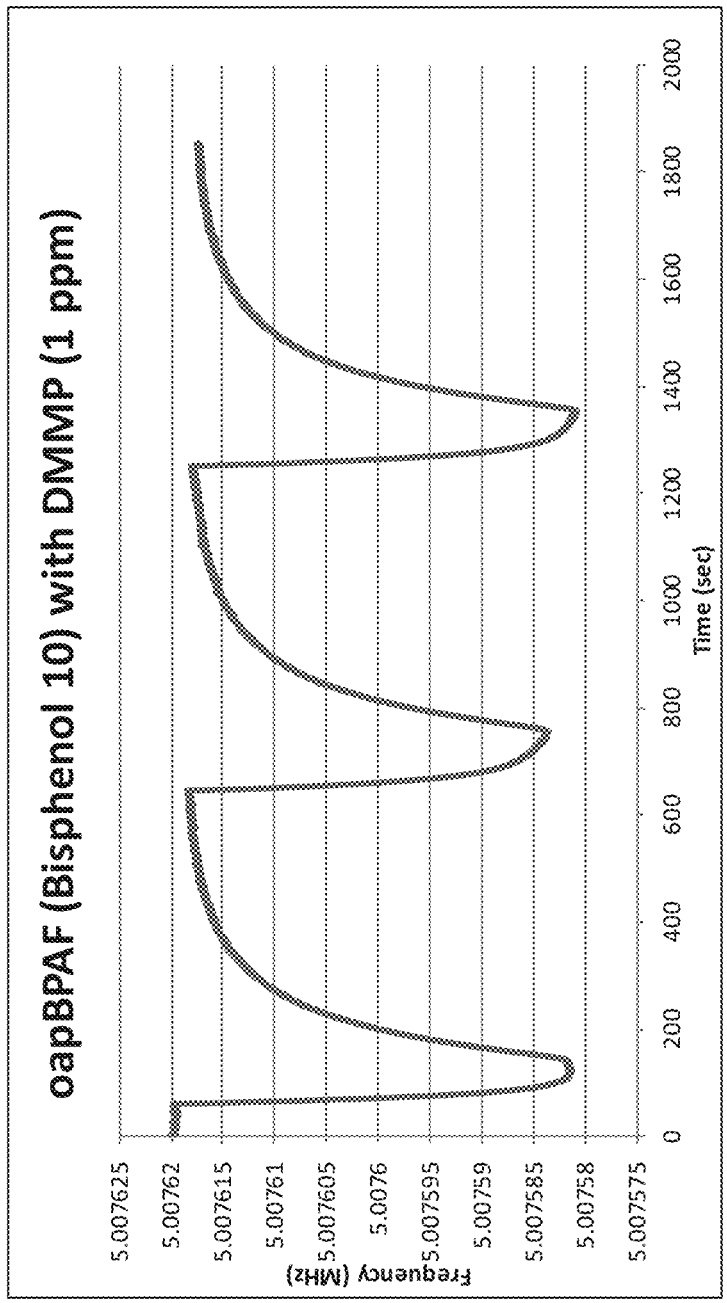
Figure 10:
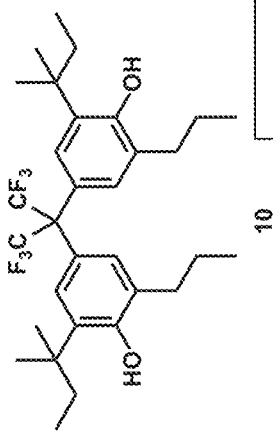
FIG. 10 is a normalized graph of the response of a QCM sensor coated with bisphenol 10 to DMMP vapor at a concentration of 1 ppm.
Figure 10:
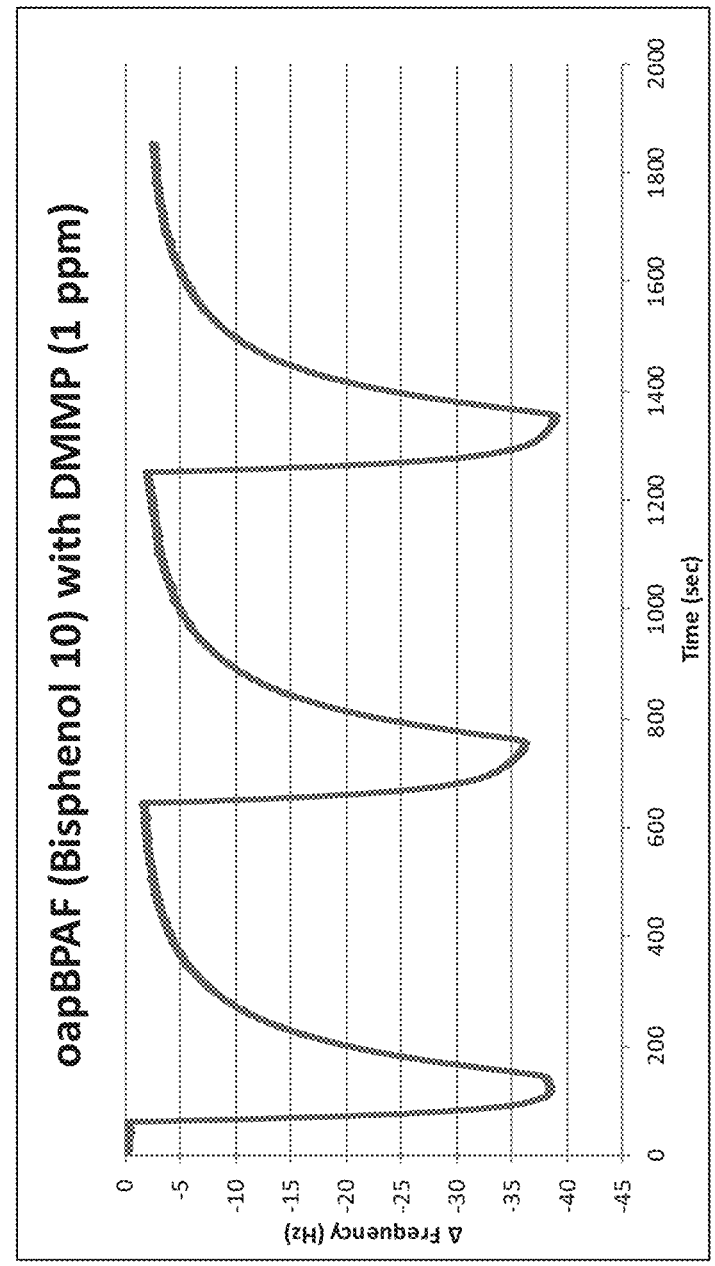

For example, FIGS. 7, and 9-10 provide sample infrared (IR) spectra and Quartz Crystal Microbalance (QCM) gravimetry data, respectively. FIGS. 7, 9, and 10 show IR spectra for vapor-sorbent binding and signal response data for a sorbent 10-coated QCM exposed to an example vapor, dimethyl methylphosphonate (DMMP) vapor. DMMP is used as a nerve agent gas simulant, as are trimethyl phosphate (TMP), and diisopropyl methylphosphonate (DIMP). The IR spectrum of bisphenol 10 before exposure to DMMP vapors, when interacting with DMMP vapors, and after the DMMP has been purged from the system are shown. While interacting with the DMMP, the IR spectrum shows that there is a clear decrease in the hydroxyl absorption frequency ($\sim$3650 cm$^{-1}$) and a new, broad hydrogen-bonded hydroxyl frequency ($\sim$3300 cm$^{-1}$). After the DMMP is purged, the IR spectrum has returned to its initial, pre-exposure state, with the sharp hydroxyl peak reforming. The QCM sensor, containing a crystal coated with bisphenol 10, demonstrates mass uptake upon exposure to DMMP vapor, as evidenced by a pronounced frequency change. After removing the DMMP source and flowing clean air over the QCM sensor, the signal returns to the original baseline, corresponding to the reversible removal of DMMP from the sorbent. In some aspects of the invention, the sorbent molecules exhibit at least a 50% reduction in infrared spectral signal for the associated hydroxyl groups as compared to sorbent molecules not substituted with the bisphenol steric group or groups.

Figure 8:
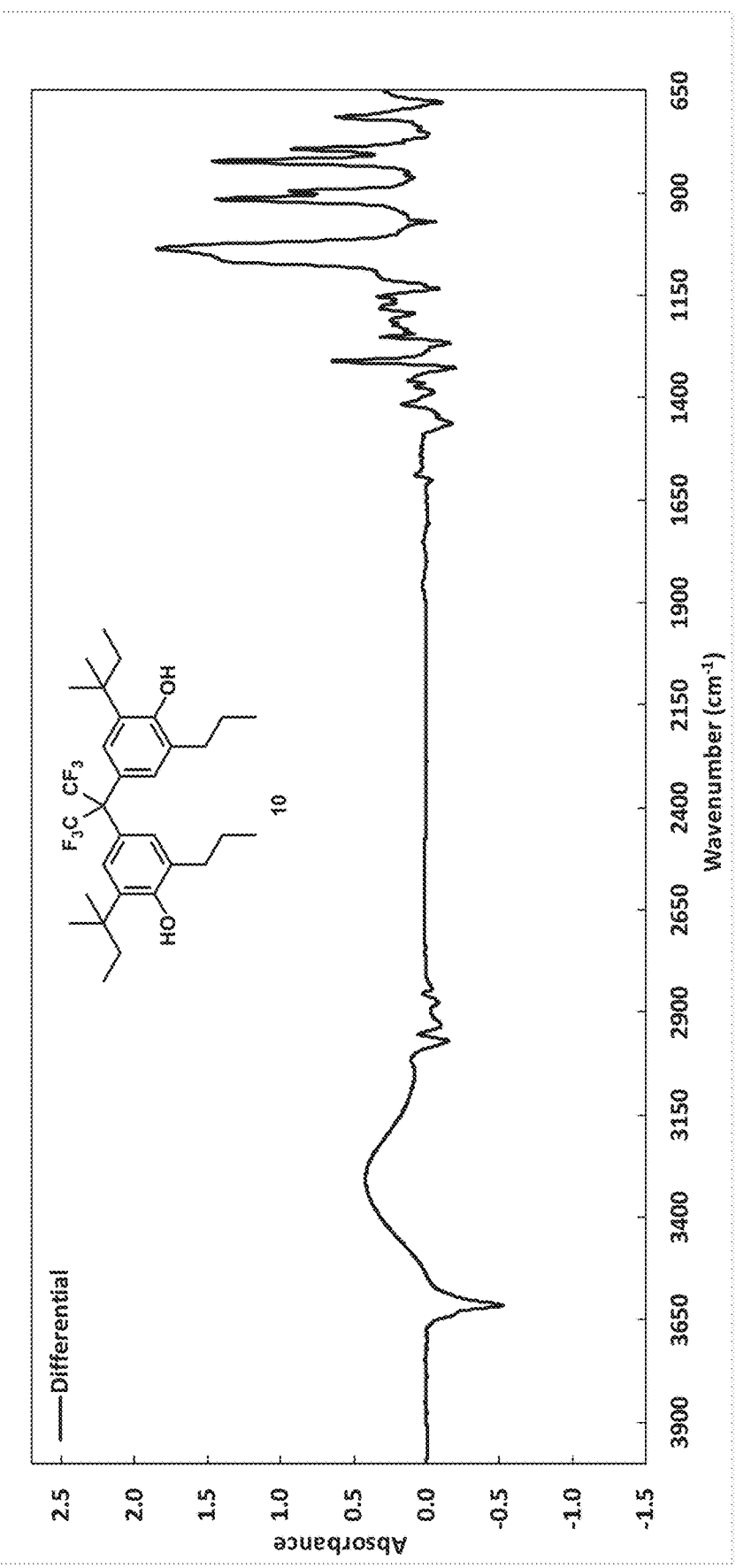
FIG. 8 shows the differential IR spectrum of bisphenol sorbent 10 interacting with DMMP vapor.

FIG. 8 shows the differential IR spectrum of bisphenol sorbent 10 interacting with DMMP vapors. The initial, sharp hydroxyl peak of 10 disappears (indicated by the negative peak at $\sim$3650 cm$^{-1}$) upon exposure to DMMP. A new, broad peak appears at 3300 cm$^-$.

FIG. 9 shows the response of a QCM sensor coated with bisphenol 10 to DMMP vapors at a concentration of 1 ppm. The frequency change observed (y-axis) indicates mass (DMMP vapor) uptake. The experiment was run in triplicate to demonstrate reproducibility.

FIG. 10 is a normalized graph of the response of a QCM sensor coated with bisphenol 10 to DMMP vapors at a concentration of 1 ppm. The y-axis is shown in Hz, with the maximum frequency set to 0 to show absolute frequency change. The frequency change observed (y-axis) indicates mass (DMMP vapor) uptake. The experiment was run in triplicate to demonstrate reproducibility. As an alternative to the QCM sensor, a microcantilever device or other gravimetry sensing apparatus may be used.

The bisphenol sorbents of the invention may be used in accordance with methods for detecting analytes that include one or more hydrogen-bond basic groups. These methods include providing one or more of the bisphenol sorbents of the invention, which may optionally be incorporated onto or into a support material or structure. The bisphenol sorbents are then contacted with a sample that may contain one or more analytes of interest. When the analyte of interest is present, the bisphenol sorbent selectively binds with the analyte(s) of interest to form a bisphenol sorbent-analyte physisorption type bond. Due to the presence of the steric groups, the bisphenol sorbent is only able to bind with analytes that have a small enough size to circumvent the steric groups. Further selectivity is achieved due to the fact that the strong hydrogen-bond acid groups preferentially bind to strong hydrogen-bond basic groups. This prevents false detection due to binding with more weakly basic interferents such as aromatic based fuels.

The detection methods of the invention may be combined with existing IR spectroscopy and mass-sensitive detection techniques in order to determine the composition of the bound analyte.

In addition to detection methods, the invention provides methods in which one or more of the bisphenol sorbents of the invention are used for collecting analytes that have one or more hydrogen-bond basic groups. Analytes that may be collected include toxic or hazardous chemicals, such as CWAs, TICS, and explosives. A layer of bisphenol sorbent may be provided, for example, by immobilizing the bisphenol sorbent on a support structure, or within the pores of a porous support structure. The bisphenol sorbent is then contacted with a sample that contains the analyte to be collected. The bisphenol sorbent selectively binds with the stronger hydrogen-bond basic analyte as compared to any weaker hydrogen-bond basic chemicals or interferents that may be present. The bisphenol sorbent-analyte interaction may be defeated by heating, releasing the analyte, and permitting the bisphenol sorbent layer to be re-used for further collections. The collection methods may be used, for example, with Solid Phase MicroExtraction (SPME) fibers.

The bisphenol sorbents may also be used in methods for conducting chromatographic separation of mixtures of compounds including analytes having one or more hydrogen-bond basic groups. The bisphenol sorbents of the invention are provided on a chromatography stationary phase, and then contacted with a sample that includes a hydrogen-bond basic compound. The bisphenol sorbent selectively binds with hydrogen-bond basic analytes having higher hydrogen-bond basicity, and any chemicals or interferents having lower hydrogen-bond basicity that are present in the sample are separately eluted through the chromatographic column.

The bisphenol sorbents of the invention may also be beneficially used in methods to prevent or reduce endocrine disruption that may be caused when unreacted bisphenols are ingested by humans and animals, when used in the place of conventional bisphenols not incorporating the steric protection groups of the invention. The invention also provides methods for protecting the hydroxyl groups of bisphenols with the steric groups of the invention.

Conventional bisphenols, such as bisphenol S (CAS 80-09-1), bisphenol C2 (CAS 14868-03-2), bisphenol A (CAS 80-05-7), bisphenol AP (CAS 1571-75-1), bisphenol B (CAS 77-40-7), bisphenol BP (CAS 1844-01-5), bisphenol C (CAS 79-97-0), bisphenol E (CAS 2081-08-5), bisphenol F (CAS 620-92-8), bisphenol G (CAS 127-54-8), bisphenol M (CAS 13595-25-0), bisphenol P (CAS 2167-51-3), bisphenol TMC (CAS 129188-99-4), and bisphenol Z (CAS 843-55-0) are often used to make articles formed from polycarbonate plastics, epoxy resins, and polyvinyl chloride. Bisphenol A and Bisphenol S monomers in particular, for example, have been shown to cause endocrine disruption in humans and animals that ingest foods and liquids packaged in, or otherwise exposed to, plastics made using bisphenol monomers. Without wishing to be bound by theory, it is believed that the endocrine disruption is caused when residual bisphenol monomers in the plastics mimic the hormone estrogen and bind to its receptors in the body. These reports of endocrine disruption have resulted in efforts to reduce their use in plastics that are used to contain foods and liquids for human and/or animal consumption.

The formed polymeric articles may include a quantity of unreacted bisphenol monomer, which can migrate out of the formed polymer over its useful life. In addition, as the formed polymer degrades, additional bisphenol monomer may be released from the polymeric article. For example, bisphenols may diffuse out of a polymeric article at a higher rate due to polymer degradation caused by exposure to high temperature (i.e., especially temperatures of about 100° C. or greater), pH (i.e., alkaline conditions), and UV light.

The methods of the invention for reducing or eliminating endocrine disruption caused by the presence of bisphenols include forming a polymeric article by polymerizing a reaction mixture comprising a bisphenol monomer of Formula A or Formula B, as described above. The reaction mixture may also include one or more chemicals used to produce the polycarbonate plastics, epoxy resins, or polyvinyl chloride. These include, but are not limited to, phosgene, epichlorohydrin, catalysts, plasticizers, and stabilizers.

After the polymeric article is formed using the bisphenol monomers of Formula A or Formula B, any unreacted bisphenol monomers or any bisphenol monomers that may be released due to degradation of the polymer beneficially exhibit reduced levels of endocrine disruption as compared to a polymeric article formed by polymerizing a reaction mixture comprising conventional bisphenol monomers, or any other bisphenol not substituted with the steric groups of the invention to protect the acidic hydrogen bonds at the hydroxyl groups.

It is believed that any protected bisphenol monomers of the invention that are present in an article, such as an article formed from polycarbonate, epoxy, or PVC, are beneficially hindered from binding with hormone and other receptors in the body. The bioactivity of the bisphenols of the invention may be reduced or eliminated, while still retaining their beneficial polymerization properties, allowing them to be more safely incorporated into plastic articles, including those used for containing food and drink for consumption by humans and animals.

EXAMPLES

The invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as e suited to the particular use contemplated.

Example 1

Experimental Synthetic Procedures:

Reactions were carried out in flame-dried glassware under a nitrogen atmosphere using freshly distilled solvents unless otherwise noted. Reagents were purchased from Sigma-Aldrich, Alfa Aesar, Acros, or Oakwood and used without further purification. Unless otherwise stated, reactions were conducted at room temperature (approximately 23° C.). Reactions were monitored by thin-layer chromatography (TLC) using Merck silica gel 60 $F_{254}$ (0.5 mm thickness) TLC plates followed by UV visualization and staining with iodine, potassium permanganate, vanillin, or Hanessian's stain. Flash chromatography was performed using Silicagel LC60A (60 Å, 40-63 µm) from Oakwood Chemical. $^{1}$H NMR spectra were recorded on a Bruker ASCEND™ spectrometer (400 MHz) and are reported in parts per million (ppm, δ). Splitting patterns are designated by: s, singlet; d, doublet; t, triplet; m, multiplet; b, broad. $^{1}$H NMR chemical shifts are referenced to the residual solvent peak 7.26 ppm for $CDCl_3$ and 2.05 ppm for $(CD_3)_2CO$. $^{13}$C NMR spectra were acquired on a Bruker ASCEND™ spectrometer (100 MHz) and are reported in parts per million (ppm, δ). $^{13}$C data are referenced to the residual solvent peak 77.91 ppm for $CDCl_3$ and 206.26 ppm for $(CD_3)_2CO$. Mass spectra (GC-MS) were acquired on an Agilent 5975 inert XL mass selective detector (EI) equipped with a RESTEK RTX®-5 column (CROSSBOND® 5% diphenyl/95% dimethyl poly-

Example 2

4,4'-[2,2,2-Trifluoro-1-(trifluoromethyl)ethylidene] bis[2,6-diisopropylphenol] (2)

Concentrated sulfuric acid (12.4 mL, 233 mmol, 15.6 equiv) was added to water (0.86 mL, 47.7 mmol, 3.2 equiv) at 5° C. 4,4'-(Hexafluoroisopropylidene)diphenol (Bisphenol AF, 5.0 g, 14.9 mmol, 1.0 equiv) was added and the solution turned pink. Isopropyl alcohol (5.7 mL, 74.4 mmol, 5.0 equiv) was added to the solution, a reflux condenser was attached, and the solution was heated to 60° C. for 3 h. Upon cooling, the solution was diluted with chloroform (50 mL) and water (50 mL), and the aqueous layer was extracted with chloroform (3×20 mL). The combined organic layers were extracted with saturated aqueous sodium bicarbonate (2×25 mL) and brine (1×25 mL), dried over anhydrous magnesium sulfate ($MgSO_4$), and the solvent was removed under reduced pressure. The resulting residue was purified via flash column chromatography on silica gel (3-6% ethyl acetate/hexanes) to afford the bisphenol 2 as a viscous yellow oil (1.51 g, 27%); $R_f$ 0.23 (10% ethyl acetate/hexanes). Bisphenol 2 appears to be an unstable compound and decomposes over time in the presence of light/oxygen, turning a black color. $^1$H NMR ($CDCl_3$, 400 MHz) δ 7.04 (s, 4H), 3.13 (sept, J=6.8 Hz, 4H), 1.21 (s, 12H), 1.19 (s, 12H); GC-MS (m/z): 504 (M).

Example 3

4,4'-[2,2,2-Trifluoro-1-(trifluoromethyl)ethylidene] bis[2,6-di-tert-butylphenol] (3)

To a 20 mL dram vial was added 4,4'-(hexafluoroisopropylidene)diphenol (1.00 g, 2.97 mmol, 1.0 equiv), tert-butyl alcohol (1.71 mL, 17.8 mmol, 6.0 equiv), and sulfuric acid (0.6 mL). The solution was allowed to stir for 24 h. The solution was diluted with water (3 mL) and the organic layer was extracted with ethyl acetate (3×2 mL). The combined organic layers were washed with brine (1×3 mL), dried over anhydrous $MgSO_4$, and the solvent was removed under reduced pressure. The crude residue was purified via flash column chromatography on silica gel (3-50% ethyl acetate/hexanes) to afford the bisphenol 3 as a white solid (39 mg, 2.3%). $^1$H NMR [$(CD_3)_2CO$, 400 MHz] δ: 7.22 (s, 4H), 6.43 (s, 2H), 1.39 (s, 36H); GC-MS (m/z): 560 (M).

Example 4

4,4'-(Perfluoropropane-2,2-diyl)bis(((3-methylbut-2-en-1-yl)oxy)benzene) (4)

To a solution of 4,4'-(hexafluoroisopropylidene)diphenol (5.0 g, 14.9 mmol, 1.0 equiv) in anhydrous acetone (7.1 mL) was added potassium carbonate (5.3 g, 38.7 mmol, 2.6 equiv), and the solution was allowed to stir for 30 min. 3,3-Dimethylallyl bromide (4.3 mL, 37.2 mmol, 2.5 equiv) was added dropwise and the solution was allowed to stir for 16 h. The mixture was filtered to remove remaining solids and the solvent was removed under reduced pressure. The residue was dissolved in diethyl ether, washed with brine (10 mL), and dried over anhydrous $MgSO_4$. The solvent was removed under reduced pressure to afford the ether 4 as a yellow oil (7.02 g, 100%). $^1$H NMR ($CDCl_3$, 400 MHz) δ: 7.29 (d, J=8.8 Hz, 4H), 6.88 (d, J=9.2 Hz, 4H), 5.50 (tqq, J=6.8, 1.6, 1.6 Hz, 2H), 4.52 (d, J=6.8 Hz, 4H), 1.81 (s, 6H), 1.75 (s, 6H). GC-MS (m/z): 472 (M).

Example 5

4,4'-(Perfluoropropane-2,2-diyl)bis(2-(2-methylbut-3-en-2-yl)phenol) (6)

To a ChemGlass pressure vessel was added a stir bar, 4,4'-(perfluoropropane-2,2-diyl)bisq(3-methylbut-2-en-1-yl)oxy)benzene) 4 (431 mg, 0.912 mmol, 1.0 equiv), hexamethyldisilazane (0.83 mL, 3.96 mmol, 4.3 equiv), and N,N-diethylaniline (1.8 mL). The vessel was sealed and heated to 200° C. for 42 h. The reaction was allowed to cool to room temperature and diluted with ethyl acetate (10 mL). The solution was extracted with HCl (3.0 M, 3×3 mL), washed with saturated aqueous sodium bicarbonate (2×3 mL) and brine (3 mL), and dried over anhydrous sodium sulfate ($Na_2SO_4$). The solvent was removed under reduced pressure to afford the silyl ether 5, a brown oil, which was carried forward to the desilylation without purification. GC-MS (m/z): 616 (M).

To a solution of the crude silyl ether 5 (0.912 mmol, 1.0 equiv) in tetrahydrofuran (THF, 4.6 mL) was added tetra-butylammonium fluoride (1.0 M solution in THF, 3.2 mL, 3.2 mmol, 3.5 equiv) dropwise. The solution was allowed to stir for 16 h and then quenched with brine (5 mL). The aqueous layer was extracted with diethyl ether (3×3 mL). The combined organic layers were washed with saturated aqueous ammonium chloride (5 mL) and brine (5 mL), dried over anhydrous $MgSO_4$, and the solvent was removed under reduced pressure. The resulting residue was purified via flash column chromatography on silica gel (5-17% ethyl acetate/hexanes) to afford the alkene 6 as a viscous pale yellow oil (196 mg, 45% over 2 steps); $R_f$ 0.13 (10% ethyl acetate/hexanes). $^1$H NMR ($CDCl_3$, 400 MHz) δ: 7.23 (m, 4H), 6.82 (dd, J=7.2, 2.0 Hz, 2H), 6.19 (dd, J=17.6, 10.4 Hz, 2H), 5.98 (s, 2H), 5.36 (dd, J=17.6, 0.8 Hz, 2H), 5.33 (dd, J=10.4, 0.8 Hz, 2H), 1.35 (s, 12H). GC-MS (m/z): 472 (M).

Example 6

4,4'-(Perfluoropropane-2,2-diyl)bis(2-(tert-pentyl) phenol) (7)

In a glove box, palladium on carbon (10%, 34 mg, 31.9 μmol, 8 mol % Pd) was added to a round-bottom flask. The flask was removed from the glove box and placed under a nitrogen atmosphere. Ethanol (4.2 mL) and 4,4'-(perfluoropropane-2,2-diyl)bis(2-(2-methylbut-3-en-2-yl)phenol) 6 (196 mg, 0.415 mmol, 1.0 equiv) were added to the flask. The nitrogen atmosphere was then replaced with a hydrogen balloon and the solution was allowed to stir for 36 h. The reaction mixture was then filtered over a pad of Celite, flushed with ethanol, and the solvent was removed by rotary evaporation. The crude reaction mixture was purified via flash column chromatography on silica gel (17% ethyl acetate/hexanes) to afford the bisphenol 7 as a viscous, pale yellow oil (191 mg, 97% yield); $R_f$ 0.33 (20% ethyl acetate/hexanes). $^1$H NMR ($CDCl_3$, 400 MHz) δ: 7.16 (d, J=8.8 Hz, 2H), 7.11 (s, 2H), 6.63 (d, J=8.8 Hz, 2H), 4.88 (s, 2H), 1.79 (q, J=7.6 Hz, 4H), 1.25 (s, 12H), 0.60 (t, J=7.6 Hz, 6H). GC-MS (m/z): 476 (M).

Example 7

4,4'-(Perfluoropropane-2,2-diyl)bis(1-(allyloxy)-2-(tert-pentyl)benzene) (8)

To a dram vial containing 4,4'-(perfluoropropane-2,2-diyl)bis(2-(tert-pentyl)phenol) 7 (70 mg, 0.147 mmol, 1.0 equiv) was added anhydrous acetone (0.3 mL) and potassium carbonate (134 mg, 0.970 mmol, 6.6 equiv). The solution was allowed to stir for 30 min, and then allyl bromide (80 µL, 0.924 mmol, 6.3 equiv) was added. After the solution was allowed to stir for 2 h, thin-layer chromatography (20% ethyl acetate/hexanes) indicated the reaction was incomplete. Acetone (1.0 mL), potassium carbonate (65 mg, 0.470 mmol, 3.2 equiv), and allyl bromide (40 µL, 0.462 mmol, 3.1 equiv) were added and the solution was allowed to stir for an additional 12 h. The mixture was filtered to remove remaining solids and the solvent was removed under reduced pressure. The residue was dissolved in diethyl ether, washed with brine (5 mL), and dried over anhydrous $MgSO_4$. The solvent was removed by rotary evaporation to afford the ether 8 as a viscous, pale yellow oil (64 mg, 78% yield). $^1$H NMR ($CDCl_3$, 400 MHz) δ: 7.27 (s, 2H), 7.11 (s, 2H), 6.81 (d, J=8.8 Hz, 2H), 6.09 (ddt, J=17.2, 10.4, 5.2 Hz, 2H), 5.44 (ddt, J=17.2, 3.2, 1.6 Hz, 2H), 5.29 (ddt, J=10.4, 2.8, 1.6 Hz, 2H), 4.58 (ddd, J=5.2, 1.6, 1.6 Hz, 4H), 1.81 (q, J=7.2 Hz, 4H), 1.23 (s, 12H), 0.56 (t, J=7.2 Hz, 6H).

Example 8

4,4'-(Perfluoropropane-2,2-diyl)bis(2-allyl-6-(tert-pentyl)phenol) (10)

To a scintillation vial containing 4,4'-(perfluoropropane-2,2-diyl)bis(1-(allyloxy)-2-(tert-pentyl)benzene) 8 (61 mg, 0.110 mmol, 1.0 equiv) was added N,N-diethylaniline (0.22 mL). The solution was heated to 200° C. and allowed to stir for 40 h. The solution was allowed to cool to room temperature and diluted with ethyl acetate (5 mL). The mixture was extracted with HCl (3.0 M, 3×3 mL), washed with saturated aqueous sodium bicarbonate (2×2 mL) and brine (3 mL), and dried over anhydrous $Na_2SO_4$. The solvent was removed by rotary evaporation to afford the alkene 9 as a brown oil, which was carried forward to the hydrogenation without further purification. $^1$H NMR ($CDCl_3$, 400 MHz) δ: 7.05 (s, 2H), 7.04 (s, 2H), 6.01 (ddt, J=16.4, 10.4, 6.0 Hz, 2H), 5.29 (s, 2H), 5.23 (ddt, J=10.4, 3.2, 1.6 Hz, 2H), 5.18 (ddt, J=17.2, 3.2, 1.6 Hz, 2H), 3.39 (ddd, J=6.0, 1.6, 1.6 Hz, 4H), 1.79 (q, J=7.6 Hz, 4H), 1.25 (s, 12H), 0.58 (t, J=7.6 Hz, 6H).

In a glove box, palladium on carbon (10%, 25 mg, 23.5 µmol, 21 mol % Pd) was added to a round-bottom flask, which was then removed from the glovebox and placed under a nitrogen atmosphere. The crude alkene 9 (61 mg, 0.110 mmol, 1.0 equiv) and ethanol (2.1 mL) were added to the flask. The nitrogen atmosphere was then replaced with a hydrogen balloon and the solution was allowed to stir for 60 h. The reaction mixture was then filtered over a pad of Celite, flushed with ethanol, and the solvent was removed by rotary evaporation. The crude residue was purified via flash column chromatography on silica gel (4% ethyl acetate/hexanes) to afford the bisphenol 10 as a viscous, pale yellow oil (29 mg, 47% over 2 steps); $R_f$ 0.40 (10% ethyl acetate/hexanes). $^1$H NMR ($CDCl_3$, 400 MHz) δ: 7.04 (s, 2H), 7.00 (s, 2H), 4.95 (s, 2H), 2.52 (t, J=7.6 Hz, 4H), 1.80 (q, J=7.2 Hz, 4H), 1.61 (tq, J=7.6, 7.6 Hz, 4H), 1.26 (s, 12H), 0.95 (t, J=7.2 Hz, 6H), 0.60 (t, J=7.6 Hz, 6H). GC-MS (m/z): 560 (M).

Example 9

4,4'-(Perfluoropropane-2,2-diyl)bis(1-(allyloxy)-2-propylbenzene) (12)

To a scintillation vial containing 2,2-bis(4-hydroxy-3-propylphenyl)hexafluoropropane[1] 11 (349 mg, 0.830 mmol, 1.0 equiv) was added anhydrous acetone (1.5 mL) and potassium carbonate (607 mg, 4.39 mmol, 5.3 equiv). The solution was allowed to stir for 30 min, and then allyl bromide (0.36 mL, 4.16 mmol, 5.0 equiv) was added. After the reaction was allowed to stir for 2.5 h, thin-layer chromatography (20% ethyl acetate/hexanes) indicated the reaction was still incomplete. Potassium carbonate (596 mg, 4.31 mmol, 5.2 equiv) and ally bromide (0.36 mL, 4.16 mmol, 5.0 equiv) were added and the reaction was allowed to stir for an additional 16 h. The mixture was filtered to remove remaining solids and the solvent was removed under reduced pressure. The residue was dissolved in diethyl ether, washed with brine (5 mL), and dried over anhydrous $MgSO_4$. The solvent was removed by rotary evaporation to afford the ether 12 as a viscous, pale yellow oil (331 mg, 80%). $^1$H NMR ($CDCl_3$, 400 MHz) δ: 7.20 (d, J=8.4 Hz, 2H), 7.08 (s, 2H), 6.78 (d, J=8.8 Hz, 2H), 6.06 (ddt, J=17.2, 10.4, 4.8 Hz, 2H), 5.44 (ddt, J=17.2, 3.2, 1.6 Hz, 2H), 5.28 (ddt, J=10.4, 3.2, 1.6 Hz, 2H), 4.56 (ddd, J=4.8, 1.6, 1.6 Hz, 4H), 2.57 (t, J=7.6 Hz, 4H), 1.56 (tq, J=7.6, 7.6 Hz, 4H), 0.88 (t, J=7.6 Hz, 6H).

Example 10

4,4'-(Perfluoropropane-2,2-diyl)bis(2-allyl-6-propylphenol) (14)

To a ChemGlass pressure vessel was added 4,4'-(perfluoropropane-2,2-diyl)bis(1-(allyloxy)-2-propylbenzene) 12 (331 mg, 0.661 mmol, 1.0 equiv) and N,N-diethylaniline (1.3 mL). The solution was heated to 200° C. and allowed to stir for 40 h. The solution was allowed to cool to room temperature and diluted with ethyl acetate (5 mL). The mixture was extracted with HCl (3.0 M, 3×3 mL), washed with saturated aqueous sodium bicarbonate (2×3 mL) and brine (3 mL), and dried over anhydrous $Na_2SO_4$. The solvent was removed under reduced pressure to afford the alkene 13 as a brown oil, which was carried forward to the hydrogenation without further purification.

In a glove box, palladium on carbon (10%, 49 mg, 46.3 µmol, 7 mol % Pd) was added to a round-bottom flask, which was then removed from the glovebox and placed under a nitrogen atmosphere. The crude alkene 13 (331 mg, 0.661 mmol, 1.0 equiv) and ethanol (6.6 mL) were added to the flask and the nitrogen atmosphere was subsequently replaced with a hydrogen balloon. The solution was allowed to stir for 60 h, filtered over a pad of Celite, and the Celite was flushed with ethanol. The solvent was removed by rotary evaporation and the crude residue was purified via flash column chromatography on silica gel (9% ethyl acetate/hexanes) to afford the bisphenol 14 as a waxy yellow solid (289 mg, 87% over 2 steps). $^1$H NMR ($CDCl_3$, 400 MHz) δ: 6.97 (s, 4H), 4.76 (s, 2H), 2.53 (t, J=7.6 Hz, 8H), 1.59 (tq, J=7.6, 7.6 Hz, 8H), 0.93 (t, J=7.6 Hz, 12H).

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A method for detecting an analyte comprising one or more hydrogen-bond basic groups, comprising:
   providing a bisphenol sorbent comprising a compound of formula I or formula II having steric groups $R^1$ and $R^2$

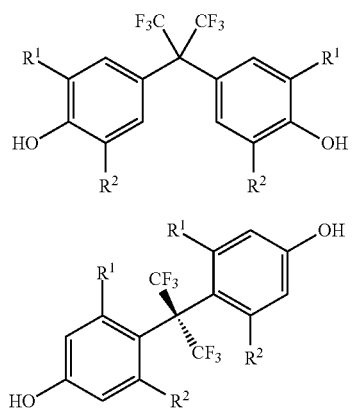

wherein
$R^1$ is selected from the group consisting of prop-1-en-2-yl;-dimethyl(phenyl)silyl; trimethylsilyl; diphenylmethyl; methylthio; prop-2-enyl; benzyl; ethylthio; cyclopropyl; 2-(trimethylsilyl)ethyl; 2,2-dimethylpropyl; 2-methylpropyl; phenylethyl; propyl; butyl; sec-butyl; pentyl; heptyl; propan-2-yl; cyclopentyl; cyclohexyl; cyclobutyl; 3-ethylpentan-3-yl; ethyl; 1,1-dimethylpropyl; (trimethylsilyl)methyl; trifluoromethyl; and fluoro; and $R^2$ is selected from the group consisting of methyl; tert-butyl; prop-1-en-2-yl; dimethyl(phenyl)silyl; trimethylsilyl; diphenylmethyl; methylthio; prop-2-enyl; benzyl; ethylthio; cyclopropyl; 2-(trimethylsilyl)ethyl; 2,2-dimethylpropyl; 2-methylpropyl; phenylethyl; propyl; butyl; sec-butyl; pentyl; heptyl; propan-2-yl; cyclopentyl; cyclobutyl; 3-ethylpentan-3-yl; ethyl; 1,1-dimethylpropyl; (trimethylsilyl)methyl; trifluoromethyl; and fluoro;

contacting the bisphenol sorbent with a sample suspected of containing an analyte comprising one or more hydrogen-bond basic groups; and detecting the analyte present in the bisphenol sorbent, wherein the bisphenol sorbent selectively binds with the analyte, whose one or more hydrogen-bond basic groups circumvent steric groups $R^1$ and $R^2$, forming a bisphenol sorbent-analyte bond.

2. The method of claim 1, wherein the analyte present in the bisphenol sorbent is detected using an optical spectroscopy technique.

3. The method of claim 1, wherein the analyte is detected using an infrared (IR) spectroscopy technique.

4. The method of claim 1, wherein the analyte is detected with gravimetry sensing.

5. The method of claim 4, wherein the gravimetry sensing is performed with a Quartz Crystal Microbalance or microcantilever device.

6. The method of claim 1, wherein the analyte is selected from the group consisting of TEA (triethylamine), TPA (tripropylamine), BuAm (butylamine), ammonia, arsines, acetone, acetonitrile, pyridine, DMSO (dimethylsulfoxide), DMMP (dimethyl methylphosphonate), TATP (triacetone triperoxide), VE (O-ethyl-S-[2-(diethylamino)ethyl] ethylphosphonothioate), VG (O,O-diethyl-S[2-(diethylamino)ethyl] phosphorothioate), VM (O-ethyl-S[2-(diethylamino)ethyl] methylphosphonothioate), VX (O-ethyl S-(2-diisopropylaminoethyl) methylphosphonothioate)), TNT (2-methyl-1,3,5-trinitrobenzene), TEX (4,10-dinitro-2,6,8,12-tetraoxa-4,10-diazatetracyclo[5.5.0.0$^{5,9}$,0$^{3,11}$]-dodecane), HMX (octahydro-1,3,5,7-tetranitro-1,3,5,7-tetrazocine), CL-20 (2,4,6,8,10,12-Hexanitro-2,4,6,8,10,12-hexaazatetracyclo[5.5.0.0$^{3,11}$0.0$^{5,9}$]dodecane), and RDX (1,3,5-trinitro-1,3,5-triazinane).

* * * * *